United States Patent [19]
Stern et al.

[11] Patent Number: 5,741,248
[45] Date of Patent: Apr. 21, 1998

[54] FLUOROCHEMICAL LIQUID AUGMENTED CRYOSURGERY

[75] Inventors: Robert G. Stern, Philadelphia; Thomas H. Shaffer, Lansdowne; Marla R. Wolfson, Philadelphia, all of Pa.

[73] Assignee: Temple University-of the Commonwealth System of Higher Education, Philadelphia, Pa.

[21] Appl. No.: 487,386

[22] Filed: Jun. 7, 1995

[51] Int. Cl.⁶ .................................................. A61B 17/36
[52] U.S. Cl. .................................................. 606/21; 606/23
[58] Field of Search .................... 606/20–26; 607/113; 62/56; 128/660.01, 660.03

[56] References Cited

U.S. PATENT DOCUMENTS

| | | |
|---|---|---|
| Re. 26,276 | 10/1967 | Hirschhorn . |
| 3,451,395 | 6/1969 | Thyberg . |
| 3,512,531 | 5/1970 | Crump et al. . |
| 3,658,066 | 4/1972 | Saidi et al. ............................ 128/303.1 |
| 3,667,248 | 6/1972 | Carlson . |
| 3,682,166 | 8/1972 | Jacobs . |
| 3,712,306 | 1/1973 | Bryne . |
| 3,786,814 | 1/1974 | Armao ................................... 128/305 |
| 3,889,680 | 6/1975 | Armao ................................... 128/303.1 |
| 4,073,879 | 2/1978 | Long, Jr. . |
| 4,285,928 | 8/1981 | Wada et al. . |

(List continued on next page.)

FOREIGN PATENT DOCUMENTS 281 212 A  8/1988  European Pat. Off. .

OTHER PUBLICATIONS

M.O. Maiwand, Medical Practice (Contemporary Themes)—Cryotherapy for advanced carcinoma of the trachea and bronchi, British Medical Journal, vol. 293 (Jul. 1986).

Thomas H. Schaffer, A brief review: liquid ventilation, Undersea Biomedical Research, vol. 14, No. 2, pp. 169–176 (Mar. 1987).

Bradley M. Rodgers, Kenneth D. Blake, and James A. Alexander, The effects of profound cryotherapy upon the pulmonary parenchyma, Profound Cryotherapy, vol. 83, No. 5, pp. 784–789 (May 1982).

G. Uhlschmid, F. Kolb, and F. Largiader, Cryosurgery of Pulmonary Metastases, Cryobiology 16, 171–178 (1979).

(List continued on next page.)

Primary Examiner—Jennifer Bahr
Assistant Examiner—Bryan K. Yarnell
Attorney, Agent, or Firm—Seidel, Gonda, Lavorgna & Monaco, PC

[57] ABSTRACT

A method for cryogenic treatment of a lesion which includes the steps of delivering a fluorochemical liquid to the lesion, placing at least one cryoprobe into the lesion, and circulating cryogenic fluid through the cryoprobe, the cryogenic fluid causing an ice ball to form in a vicinity around the cryoprobe, wherein the ice ball obliterates at least a portion of the lesion. The fluorochemical liquid is utilized to augment the cryosurgical procedure and is perfused or injected into and/or around the lesioned site prior and/or during the application of a cryoprobe to the site. In one embodiment of the invention, the fluorochemical liquid acts as a contrast agent to enhance real-time medical imaging of the lesioned area and modifies the environment in and around the lesioned area. In another embodiment of the invention, the fluorochemical liquid augments cryosurgical procedures by controlling the size and shape of ice balls formed during the cryosurgical procedures. In this embodiment, a fluorochemical liquid with a properly chosen thermal conductivity and freezing point is utilized. Depending on the thermal properties chosen, the liquid either augments freezing of the target area and/or promotes thermal conduction to freeze larger areas, or limits the freezing of the target area and reduces thermal conduction. In a non-cryoprobe embodiment, the liquid is cooled to a temperature below the freezing point of the biological tissue. The cooled liquid is then infused into or around the cystic lesion to produce ablation.

66 Claims, 21 Drawing Sheets

U.S. PATENT DOCUMENTS

| | | |
|---|---|---|
| 4,378,797 | 4/1983 | Osterholm . |
| 4,451,251 | 5/1984 | Osterholm . |
| 4,490,351 | 12/1984 | Clark, Jr. . |
| 4,657,532 | 4/1987 | Osterholm . |
| 4,661,092 | 4/1987 | Popovich et al. ............................ 604/26 |
| 4,696,297 | 9/1987 | Pleines et al. . |
| 4,781,676 | 11/1988 | Schweighardt et al. . |
| 4,795,423 | 1/1989 | Osterholm . |
| 4,865,836 | 9/1989 | Long, Jr. . |
| 4,951,673 | 8/1990 | Long . |
| 4,963,130 | 10/1990 | Osterholm . |
| 4,987,154 | 1/1991 | Long, Jr. . |
| 4,993,415 | 2/1991 | Long . |
| 5,098,428 | 3/1992 | Sandlin . |
| 5,132,089 | 7/1992 | Lightfoot . |
| 5,137,510 | 8/1992 | Van Deripe . |
| 5,149,319 | 9/1992 | Unger . |
| 5,149,321 | 9/1992 | Klatz et al. ................................ 604/52 |
| 5,150,706 | 9/1992 | Cox et al. . |
| 5,158,536 | 10/1992 | Sekins et al. . |
| 5,160,313 | 11/1992 | Carpenter et al. . |
| 5,200,170 | 4/1993 | McDow . |
| 5,200,430 | 4/1993 | Federman . |
| 5,207,220 | 5/1993 | Long . |
| 5,207,674 | 5/1993 | Hamilton et al. . |
| 5,213,570 | 5/1993 | Van Deripe . |
| 5,234,405 | 8/1993 | Klatz et al. . |
| 5,244,924 | 9/1993 | Meinert . |
| 5,279,288 | 1/1994 | Christopher . |
| 5,281,215 | 1/1994 | Milder ........................................ 606/20 |
| 5,309,903 | 5/1994 | Long . |
| 5,334,181 | 8/1994 | Rubinsky et al. ........................... 606/22 |
| 5,335,650 | 8/1994 | Shaffer . |
| 5,420,176 | 5/1995 | Unger et al. ............................. 523/205 |

OTHER PUBLICATIONS

Andrew A. Gage, Collective Review—Cryosurgery In The Treatment Of Cancer, *Surgery, Gynecology & Obstetrics*, vol. 174, pp. 73–92 (Jan. 1992).

H. Bryan Neel, III, Kenneth H. Farrell, Lawrence W. DeSanto, W. Spencer Payne, and David R. Sanderson, Cryosurgery of Respiratory Structures, pp. 1062–1071, 417–426.

Douglas Torre, Cutaneous Cryosurgery, pp. 202–209.

Andrew A. Gage., Cryosurgery for Oral and Pharyngeal Carcinoma, *The American Journal of Surgery*, vol. 118, pp. 669–672 (Nov. 1969).

Setrag A. Zacarian, "Cryosurgery in Dermatologic Disorders and in the Treatment of Skin Cancer", *Journal of Cryosurgery*, pp. 70–75.

Marla R. Wolfson & Thomas H. Shaffer, Liquid ventilation during early development: theory, physiologic processes and application, *Journal of Developmental Physiology*, 13.1–12, 1990).

T.H. Shaffer, A brief review: liquid ventilation, *Undersea Biomedical Research* vol. 14, No. 2, pp. 169–176 (Mar. 1987).

Thomas H. Shaffer, Nghia Tran, Vinod K. Bhutani and Emidio M. Sivieri, Cardiopulmonary Function in Very Preterm Lambs during Liquid Ventilation, *Pediatr. Res.*, 17:pp. 68–684 (1983).

Thomas H. Shaffer, Corinne A. Lowe, Vinod K. Bhutani and Patricia R. Douglas, Liquid ventilation: effects on pulmonary function in distressed meconium–stained lambs, *Pediatric Research, 1984 International Pediatric Research Foundation, Inc.*, vol. 18, No. 1, pp. 47–52, 1984.

John W. Sargent and Raymond J. Seffel, Properties of perflourinated liquids, *Federation Proceedings*, vol. 29, No. 5, pp. 1699–1703, Sep.–Oct., 1970.

J.C. Gilbert, G.M. Onik, W.K. Hoddick and B. Rubinsky, Real Time Ultrasonic Monitoring of Hepatic Cryosurgery, *Cryobiology* 22. 319–330 (1985).

Thanjavur S. Ravikumar, Robert Kane, Blake Cady, Roger L. Jenkins, William McDermott, Gary Onik, Melvin Clouse, Glenn Steel, Jr., Hepatic Cryosurgery With Intraoperative Ultrasound Monitoring for Metastatic Colon Carcinoma, *Archives of Surgery*, vol. 122, pp. 403–409 (Apr. 1987).

Gary Onik, John Gilbert, William Hoddick, Roy Filly, Peter Callen, Boris Rubinsky, Linda Farrel, Sonographic Monitoring of Hepatic Cryosurgery in an Experimental Animal Model, *AJR* 144, pp. 1043–1047 (May 1965).

Gary Onik, Transperineal Prostatic Cryosurgery under Transrectal Ultrasound Guidance, *Seminars in Interventional Radiology*, vol. 6, No. 2, pp. 90–96 (Jun. 1989).

Gary Onik, Barbara Porterfield, Boris Rubinsky, Jeffrey Cohen, Percutaneous Transperineal Prostate Cryosurgery Using Transrectal Ultrasound Guidance: Animal Model, *Urology*, vol. XXXVII. No. 3, pp. 277–281 (Mar. 1991).

Gary Onik, Cirrelda Cooper, Henry I. Goldberg, Albert A. Moss, Boris Rubinsky and Mark Christianson, Ultrasonic Characteristics of Frozen Liver, *Cryobiology*, 21, 321–328 (1984).

Gary Onik, Charles Cobb, Jeffrey Cohen, John Zabkar, Barbara Porterfield, US Characteristics of Frozen Prostate, *Radiology*, vol. 168, No. 3, pp. 629–632 (Sep. 1988).

Gary Onik, Boris Rubinsky, Reuben Zemel, Lance Weaver, Daniel Diamond, Charles Cobb, and Barbara Porterfield, Ultrasound–Guided Hepatic Cryosurgery in the Treatment of Metastatic Colon Carcinoma—Preliminary Results, *Cancer*, vol. 67, No. 4, pp. 901–907 (Feb. 15, 1991).

Jing Deng, Pei–Xuan Cheng, Suu–Ying Gao, and Liang–Zhen Wen, Echocardiographic Evaluation of the Valves and Roots of the Pulmonary Artery and Aorta in the Developing Fetus, *Journal of Clinical Ultrasound*, 20:3–9, pp. 3–8 (Jan. 1992).

Robert G. Devenyi, Letter to the Editor—Perfluorocarbon liquid as a surgical adjunct in the surgical repair of stage V retinopathy of prematurity, *British Journal of Ophthalmology*, May 5, 1993).

K. Kamp Mortensen and A.K. Sjølie, Retinal detachment treatment by pneumatic retinopexy, *acta ophthalmologic*, 66, pp. 187–189, (1988).

Joseph C. Maroon, Gary Onik, Matthew R. Quigley, Julian E. Bailes, Cryosurgery Re–Visited For The Removal And Destruction Of Brain, Spinal And Orbita Tumors (1993).

Giovannini M. Seitz JF, Ultrasound–guided percutaneous alcohol injection of small liver metastases. Results in 40 patients, Cancer, 73(2):294–7, Jan. 15, 1994 [Abstract].

Amin Z. Bown SG, Lees, WR, Local treatment of colorectal liver metastases: a comparison of intersititial laser photocoagulation (ILP) and percutaneous alcohol injection (PAI), Clinical Radiology, 48(3):166–71, Sep. 1993 [Abstract].

Li GH, Surgical treatment of primary liver cancer complicated with cirrhosis [Chinese], Chung–Hua Chung Liu Tsa Chih, 14(2):147–1, Mar. 1992 [Abstract].

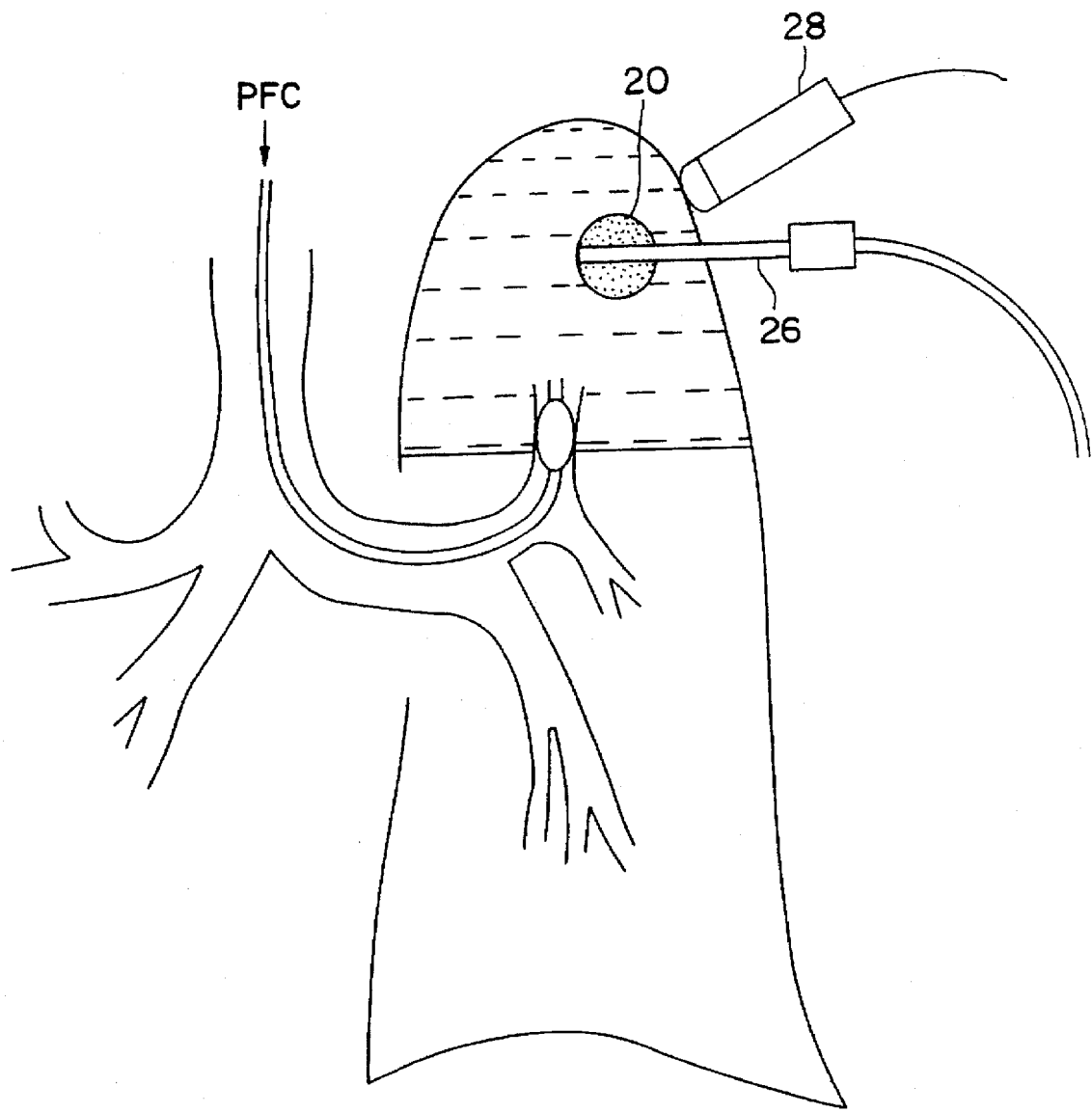
FIG. IC

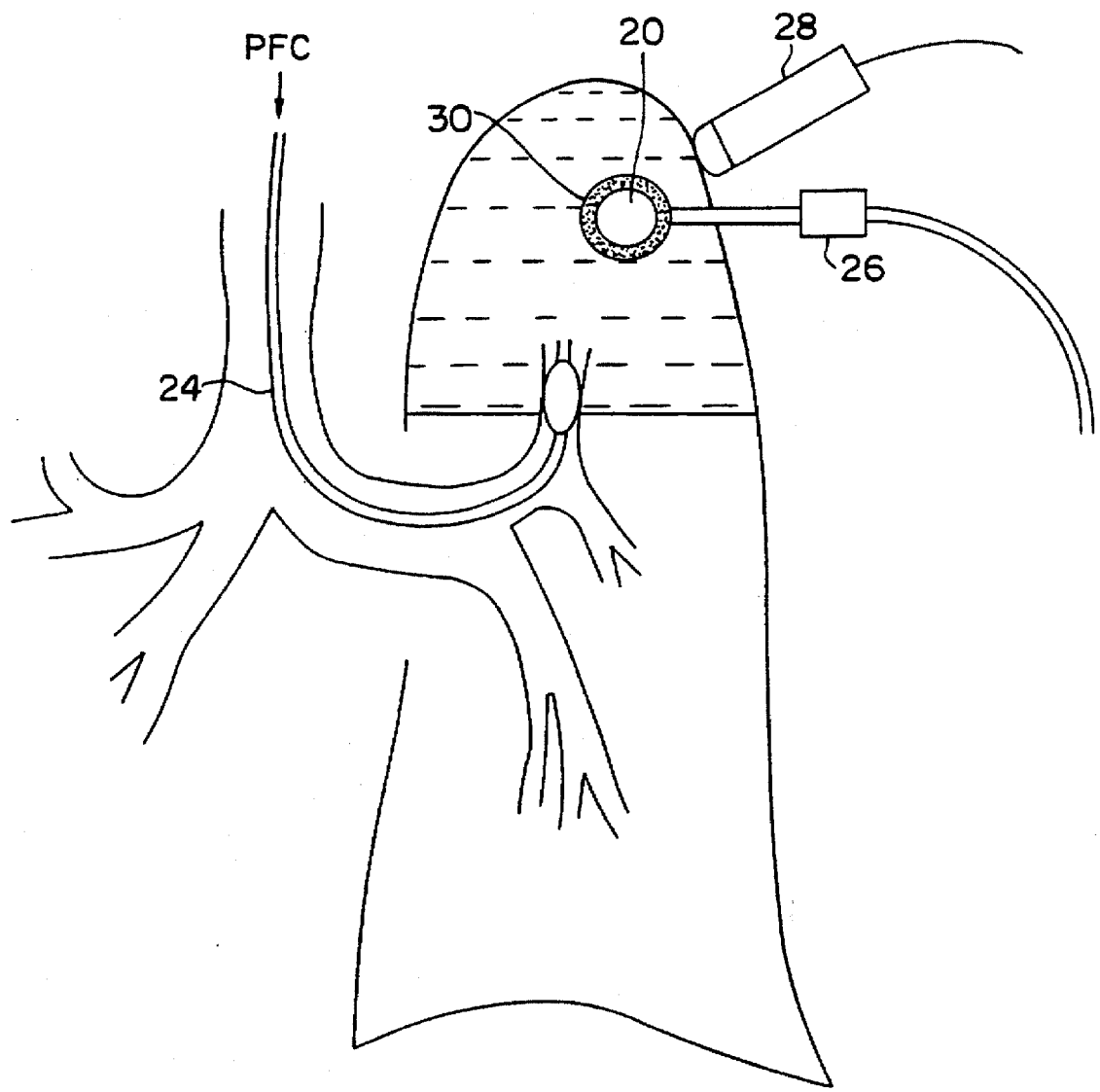
FIG. ID

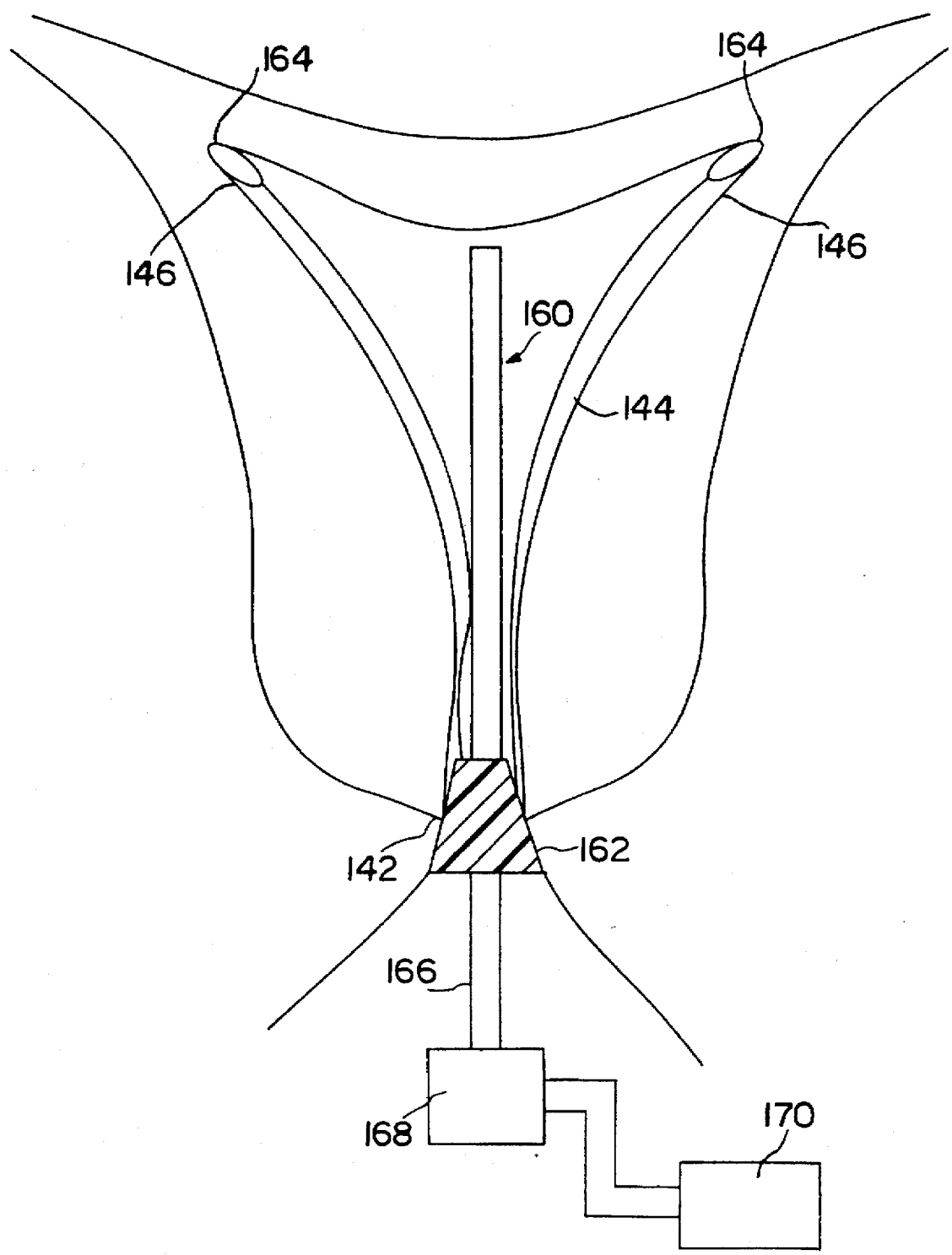
F I G. 14

FLUOROCHEMICAL LIQUID AUGMENTED CRYOSURGERY

FIELD OF THE INVENTION

This invention relates to methods and processes for performing cryosurgery using fluorochemical liquids in and around biological lesions, cysts, organs and tissue.

BACKGROUND OF THE INVENTION

Cryosurgery is the in situ destruction of living tissues through the application of low temperatures and has been used extensively in humans for a wide variety of malignancies and inflammatory disorders. The medical literature includes, but is not limited to, the following tumors and conditions that have been treated cryosurgically: carcinoma of the skin, melanoma, orbital tumors (retinoblastoma, squamous cell, melanoma), oral carcinoma, pharyngeal carcinoma, laryngeal carcinoma, tracheo-bronchial carcinoma, lung carcinoma, esophageal carcinoma, hepatic carcinoma, carcinoma of the uterus, vulva, vagina, rectum, anus, prostate, urinary bladder, penis, breast and maxillary sinus, malignant bone tumors, spinal tumors and brain tumors.

Most cryosurgery is performed using a cryoprobe or hollow tube within which a cryogenic agent (e.g., liquid nitrogen) flows in a closed loop manner. The probe is inserted into the tumor and the cryogenic agent causes circumferential freezing to occur around the probe, incorporating a given volume of frozen tissue. This creates an "ice ball" which forms to a certain size, depending upon the total time of application and the local thermal gradients. These gradients are heavily dependent on local blood flow, vascularity, adjacent structures, and other factors.

Traditionally, freezing was performed through direct visualization of tumors via a surgical or endoscopic approach with monitoring of temperatures by thermocouples placed into the tumor. This yielded less than optimal results due to inadequate thermocouple sampling and the inability to see the deep margins of a tumor. Using this methodology, it was nearly impossible to determine when and if a tumor had been completely frozen. In the early 1980's, it was discovered that real-time ultrasound (US) imaging could differentiate frozen tissue from normal tissue, and in many cases, could differentiate the tumor from normal tissue. It was subsequently learned that other medical imaging modalities including computed tomography (CT) and magnetic resonance imaging (MRI) can also distinguish frozen tissue from normal tissue. Thus, by combining imaging modalities with new cryosurgical apparatus, it was now possible to accurately direct cryoprobes into tumors and to position them appropriately to insure complete destruction of the tumor.

Additionally, it has been shown that these imaging modalities can precisely monitor the freezing process, identifying the actual margin of freezing as it passes into normal tissue. At the present time, real-time ultrasound monitoring is used in cryosurgery of prostate cancer, spinal tumors, hepatic tumors and brain tumors with excellent preliminary results.

Examples of cryosurgical techniques employing ultrasound monitoring are described in the following articles:

Onik, Gary, et at., "Sonographic Monitoring of Hepatic Cryosurgery in an Experimental Animal Model", AJR, Vol. 144, pp. 1043–1047 (May 1985).

Onik, Gary, et al., "Ultrasonic Characteristics of Frozen Liver", Cryobiology, Vol. 21, pp. 321–328 (1984).

Onik, Gary, M.D., et al., "Ultrasound-Guided Hepatic Cryosurgery in the Treatment of Metastatic Colon Carcinoma", Cancer, Vol. 67, No. 4, pp. 901–907 (Feb. 15, 1991).

Onik, Gary, M.D., et al., "Percutaneous Transperineal Prostate Cryosurgery Using Transrectal Ultrasound Guidance Animal Model", Urology, Vol. 37, No. 3, pp. 277–281 (March 1991).

Onik, Gary, M.D., et al., "US Characteristics of Frozen Prostrate", Radiology, Vol. 168, No. 3, pp. 629–631 (September 1988).

Onik, Gary, M.D., "Transperineal Prostatic Cryosurgery under Transrectal Ultrasound Guidance", Seminars in Interventional Radiology, Vol. 6, No. 2, pp. 90–96 (June 1989).

Gilbert, J. C., et al., "Real Time Ultrasonic Monitoring of Hepatic Cryosurgery" Cryobiology, Vol. 22, pp. 319–330 (1985).

Ravikumar, Thanjavur S., M.D., et al., "Hepatic Cryosurgery with Intraoperative Ultrasound Monitoring for Metastatic Colon Carcinoma", Arch Surg, Vol. 122, pp. 403–409 (April 1987).

Several significant technical problems in cryosurgery persist. One is the inability to control local thermal gradients in the area of freezing. The major physiologic contribution remains local blood flow, including the relative vascularity of the target organ and tumor. These local factors limit the volume of freezing that can occur with a given cryoprobe and also are responsible for treatment failures when tumor cells are adjacent to large heat sources such as large blood vessels. Additionally, the inability to control local thermal gradients creates difficulties in protecting adjacent structures from thermal injury, often necessitating an open surgical approach to insulate normal organs from the freezing process. This is often the case when performing hepatic cryosurgery. Furthermore, the general inability to precisely control the areas which are frozen by the cryoprobe limits the application of cryosurgery to certain procedures where this lack of control is not problematic.

Another technical problem in cryosurgery is the limitation of some imaging modalities in respect to certain organs. For example, in the lung, ultrasound cannot be used to visualize lung tumors deep in the pleural surface since the sound emitted by the ultrasound equipment will reflect off the air in the lung. In hollow organs or structures with central cavities, such as the bladder or uterus, it is necessary to distend these lumens to better visualize the extent of abnormalities when utilizing CT, MRI or US. Many tumors are identified to varying degrees by each imaging modality such that some tumor types are better evaluated overall by one particular method, yet components of the tumor or metastatic tumors may actually be better seen in a given individual using a different modality. Hence, there is a considerable need to maximize the sensitivity of imaging for effective total cryosurgical ablation of tumors.

A need, therefore, exists for improved methods of controlling and increasing the efficacy of the freezing process during cryogenic surgery and for improving the real-time visualization of the cryosurgical procedure. The current invention fills these needs.

SUMMARY OF THE INVENTION

The invention described herein employs a fluorochemical liquid to augment cryosurgical procedures involving treatment of lesions. The fluorochemical liquid is perfused or injected into and/or around the lesioned site prior to applying a cryoprobe to the site.

In one embodiment of the invention, the fluorochemical liquid acts as a contrast agent to enhance real-time medical imaging of the lesioned area and modifies the environment in and around the lesioned area.

In another embodiment of the invention, fluorochemical liquids augment cryosurgical procedures by controlling the size and shape of ice balls formed during cryosurgical procedures. In this embodiment, fluorochemical liquids which have relatively high thermal conductivities and/or relatively low freezing points, are introduced at, in and/or around the target cite. Due to their thermal properties, these liquids augment freezing of the target area and/or promote thermal conduction to freeze larger areas. For added effect, these high thermal conductivity and/or low freezing point fluorochemical liquids may optionally be cooled.

In yet another embodiment of the invention, fluorochemical liquids augment cryosurgical procedures by protecting cold-sensitive structures, which are adjacent to those locations where such procedures are being performed. In this embodiment, fluorochemical liquids having relatively low thermal conductivities are introduced either between the target area and the cold-sensitive structure to be protected or directly into the cold-sensitive structure to be protected. Due to their thermal properties, these liquids act as a shield against the freezing effects of cryosurgical procedures. For added protection, these low thermal conductivity fluorochemical liquids may optionally be heated.

In still yet another embodiment of the invention, the fluid properties of the fluorochemical liquids are employed to change the size and/or shape of a lesioned area, thereby enhancing the efficacy of the cryogenic treatment.

In another embodiment of the invention, a lung lesion is cryogenically treated by filling the lesioned area with fluorochemical liquid prior to, and during the treatment. In addition to the above-mentioned uses of the fluorochemical liquid, the fluorochemical liquid is employed, in this embodiment, to ventilate the lung.

In another embodiment of the invention, a pleural effusion or cyst is drained of any contents and replaced by fluorochemical liquid, prior to and/or during cryogenic treatment of these lesions.

In other embodiments of the invention, arterial and ductal lesions, vascular tumors and lesions in hollow structured organs are cryogenically treated by injecting or filling the lesioned site with fluorochemical liquid, prior to application of a cryoprobe thereto.

A non-cryoprobe embodiment is also disclosed wherein the fluorochemical liquid is cooled to a temperature below the freezing point of biological tissue. The cooled liquid is then delivered to and/or around the cystic lesion to produce ablation.

A preferred type of fluorochemical liquid for use in the invention is perfluorocarbon liquid, hereinafter, referred to as "PFC liquid." PFC liquids are derived from common organic compounds by the replacement of all carbonbound hydrogen atoms with fluorine atoms. PFC liquids are relatively inert, non-biotransformable, non-toxic, chemically and thermally stable, and essentially insoluble in water. They are denser than water and soft tissue and have low viscosity. They also have very low sound speeds and a high affinity for gases. Moreover, these liquids are especially suited for use in the lung embodiment due to their physiological characteristics such as: low surface tension (i.e., about 75% less than that of $H_2O$); high solubility for oxygen (i.e., about 16 times greater than that of saline); high solubility for carbon dioxide (i.e., about 3 times greater than that of saline); and relative biological inertness. Examples of PFC liquids include: Rimar™ 101 (generically known as FC-75) and RM-82, manufactured by Miteni Corp., Milano, Italy (represented in the USA by Mercantile Development Inc., Bridgetown, Conn.); Caroxin-D ($C_{10}F_{22}O_2$) and Caroxin-F ($C_9F_2O$), manufactured by Allied Chemical Corp., Morristown, N.J.; FX-80 ($C_8F_{11}O$) and FC-72, FC-75, FC-80 and FC-82, manufactured by 3M Company, St. Paul, Minn. APF-125 (perfluorodimethylcyclohexane), APF-215 (perfluoro n-butyldecalin) manufactured by Air Products; and perfluorodecalin, manufactured by Green Cross Corp., Japan.

As used herein, lesions include cysts, effusions, tumors (vascular and avascular) and the like. Additionally, when discussing the delivery of a fluorochemical liquid to a lesion, this is meant to include delivery into or in the vicinity of the lesion.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 1C shows the cryogenic surgery of the lesion in the lung according to one embodiment of the invention.

FIG. 1D shows the generation of an ice ball for ablating the lesion in the lung according to the present invention.

FIG. 14 shows a novel non-cryoprobe embodiment for use in the endometrial ablation procedure wherein cooled fluorochemical liquid is delivered to the cystic lesion.

DESCRIPTION OF THE INVENTION

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

FIGS. 1A to 1D show an improved method for cryogenically treating a lung lesion by employing a perfluorochemical liquid.

Figure 1A:
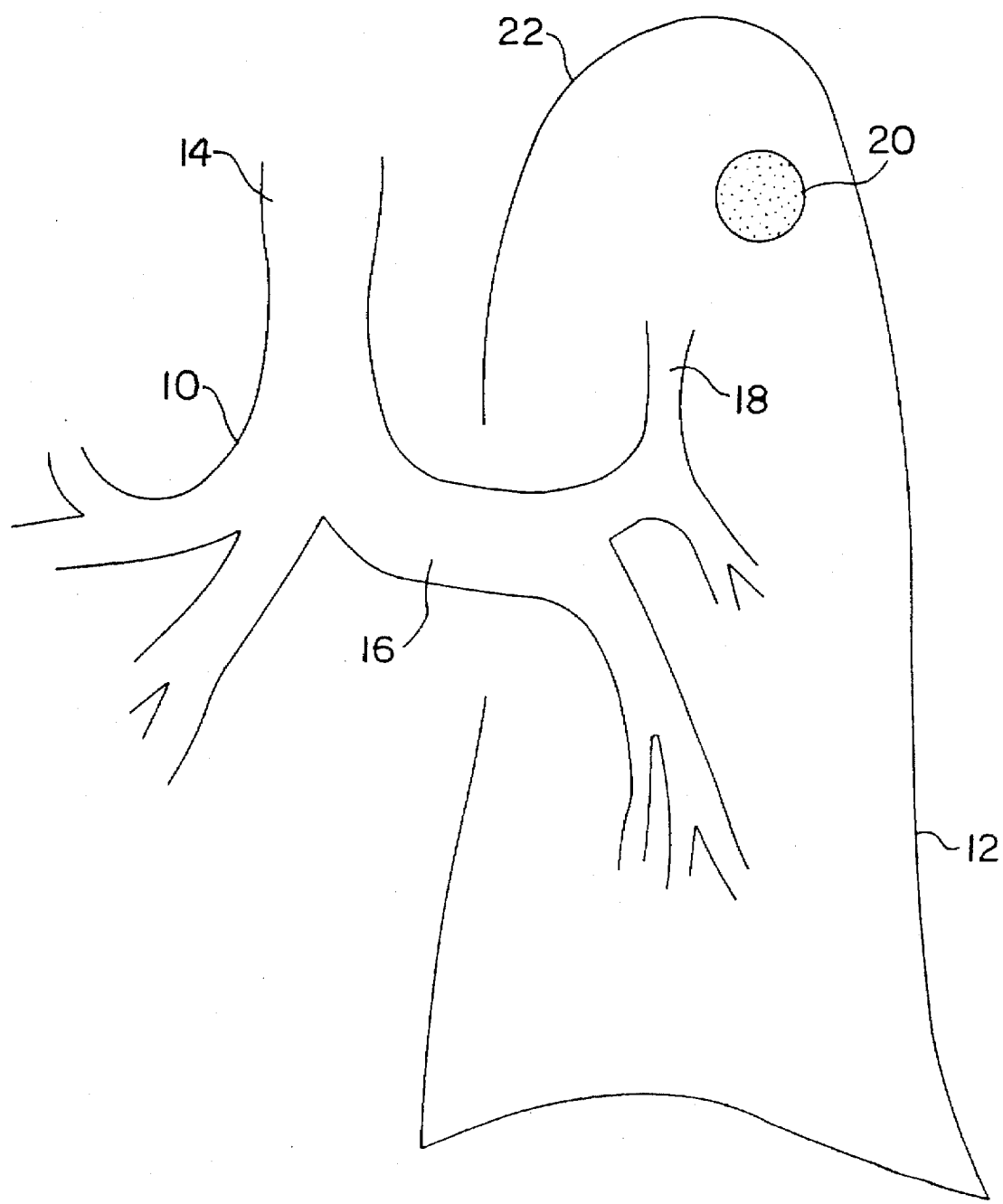
FIG. 1A illustrates a left lung with a lesion located therein.

FIG. 1A shows pulmonary pathway 10 leading to left lung 12. The pulmonary pathway 10 includes, in order, trachea 14, left mainstem bronchus 16 and left upper lobe bronchus 18. The lung 12, is illustrated with a parenchymal lesion 20 in its left upper lobe 22. Heretofore, application of cryosurgery to the lung has been limited by the inability to use ultrasound in the air-filled lung, since the ultrasound waves are reflected off air. Accordingly, the inability to monitor the surgical process effectively does not permit the focal ablation with maximal sparing of normal lung.

Figure 1B:
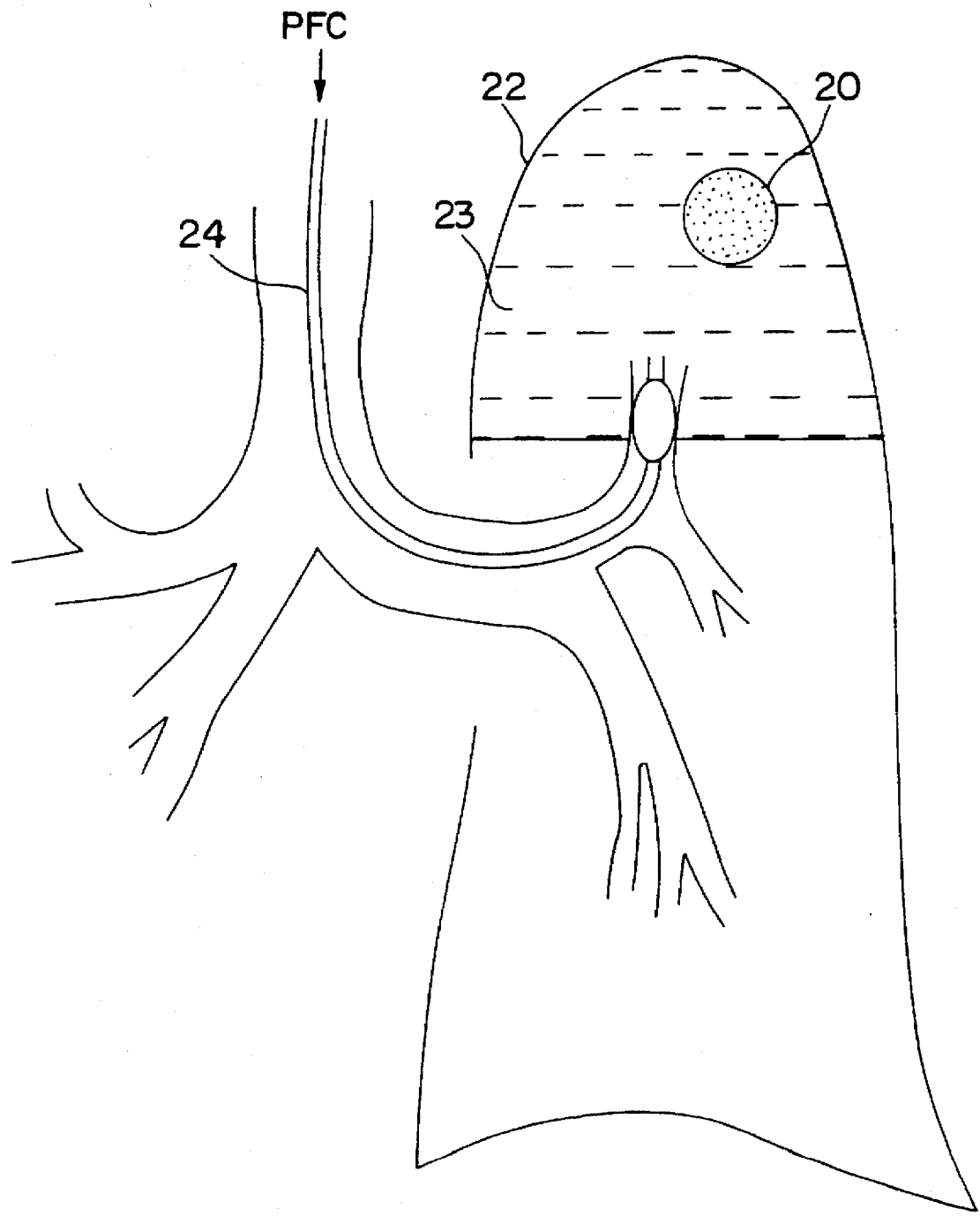
FIG. 1B illustrates a portion of the left lung filled with a fluorochemical liquid according to one embodiment of the present invention.
Figure 6:
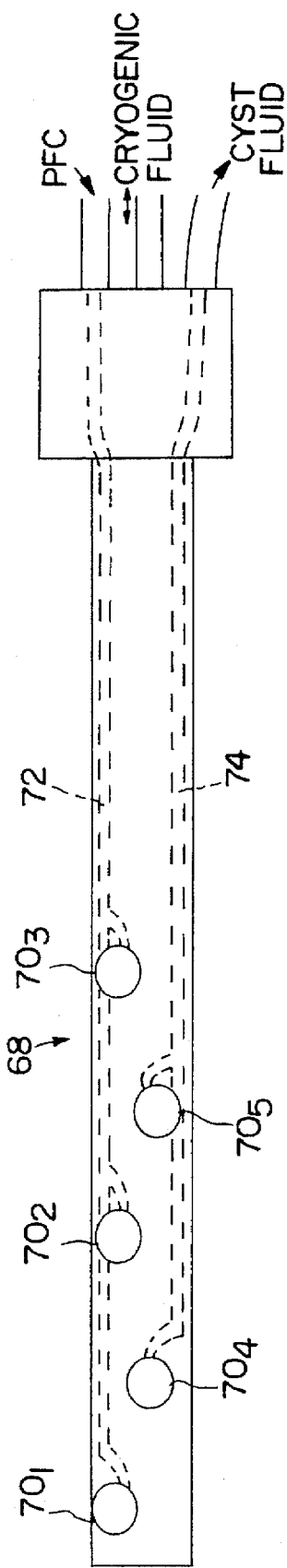
FIG. 6 is an enlarged view of the novel cryoprobe shown in FIG. 5.

FIG. 1B shows the first step in the novel cryogenic method. The lung's upper lobe 22 is filled with a PFC liquid 23. One filling technique, illustrated in FIG. 1B, is to place a balloon catheter 24 into lobar or segmental bronchus and inflate the balloon, thereby occluding the bronchial lumen. The lobe 22 is then filled with the PFC liquid through the catheter 24. The PFC 23 is, thus, effectively trapped inside the lobe 22 surrounding the lesion 20. Other filling techniques may be utilized and include selective intubation of the mainstem bronchus 16 by liquid ventilation through a conventional endotracheal tube, injection of PFC liquid through a direct puncture of the lung 12 and instillation through a modified cryoprobe having an internally or externally attached channel which allows fluid to be injected therethrough. Liquid ventilation procedures are described in U.S. Pat. Nos. 5,158,536 and 5,335,650, both of which are incorporated by reference herein. One example of a modified cryoprobe, which could be utilized for filling the lung, is illustrated in FIG. 6 and described in detail below. The uninvolved lung (i.e., the right lung) is, preferably, ventilated with oxygen.

Before proceeding to the next step, the left lung 12 is anesthetized and the lesion 20 is located using conventional fluoroscopy or ultrasound techniques, depending on the location of the lesion 20. Peripheral lesions may be located after the lung 12 is filled with PFC liquid, whereas deeper lesions may be located before filling. A prophylactic chest tube is then placed therein and a needle (not shown, but preferably 22 gauge) is placed into the lesion 20, either percutaneously or through a small thoracotomy, with subsequent placement of a guidewire (not shown). A sheath (not shown) is placed into the lesion 20 to accommodate a cryoprobe, using a traditional coaxial interventional radiologic technique. The sheath can be modeled after the Cordis sheath used for catheter exchanges. Accordingly, it will have an external membrane cover to limit leakage of the PFC liquid.

FIG. 1C shows the next step in the novel cryogenic method. Cryoprobe 26 is inserted into the sheath and down into the lesion 20 with the assistance of ultrasound monitoring by a ultrasound probe 28. Liquid nitrogen is then circulated through the cryoprobe 26, thereby causing circumferential freezing around the cryoprobe 26.

FIG. 1D shows the development of ice ball 30 in the circumferential area around the cryoprobe 26 upon the circulation of the cryogenic agent within the cryoprobe 26. The ultrasonic probe 28 is employed to monitor the ice ball formation to assure complete freezing of the lesion 20. The lesion 20 undergoes repeated freeze/thaw cycles as determined by previous studies for the most efficacious tumor ablation. As is well-known in the art, the ice ball 30 functions to obliterate the lesion 20. Once the lesion 20 is treated, the PFC liquid is drained from the lobe 22 through the balloon catheter 24, the balloon is deflated and the catheter 24, sheath and cryoprobe 26 are removed from the patient's body. The chest is then closed if the procedure was performed intraoperatively. The chest tube is typically left in place to permit drainage of any hemothorax and/or PFC liquid, since the pathology of the process is one of hemorrhagic infarction. Appropriate radiographic and biochemical monitoring is performed post-procedure.

The PFC liquid 23 performs a plurality of functions in the procedure shown in FIGS. 1A–1D. It is well-known that sound is best transmitted through fluids and that fluid-filled lungs are well imaged by ultrasound. Thus, one function of the PFC liquid 23 is to significantly improve the ultrasound image produced by displacing the air within the lung with the PFC liquid 23. Although PFC liquid is a known contrast agent which enhances ultrasound imaging (see U.S. Pat. Nos. 4,073,879, 4,285,928, 4,865,836, 4,951,673 and 4,987,154), its use during cryosurgical procedures has not, heretofore, been suggested in the prior art.

Another beneficial function of the PFC liquid is to alter the total lung volume, including the degree of lobe distension. The amount of distension can be employed to physically limit the area of freezing since this area is closely correlated to a predetermined radius from the cryoprobe 26. Thus, the size of the ice ball 30 can be partly controlled by the degree of lobe distension. The total lung volume will also affect local blood flow which has a significant effect on the freezing process. Yet another beneficial function of the PFC liquid is that it resorbs residual gases. In an alternative filling scheme wherein the PFC liquid is continuously circulated throughout the lobe 22, the PFC liquid also functions to ventilate the treated lung during the procedure. By ventilating the treated lung, respiratory motion can be suspended.

Figure 2A:
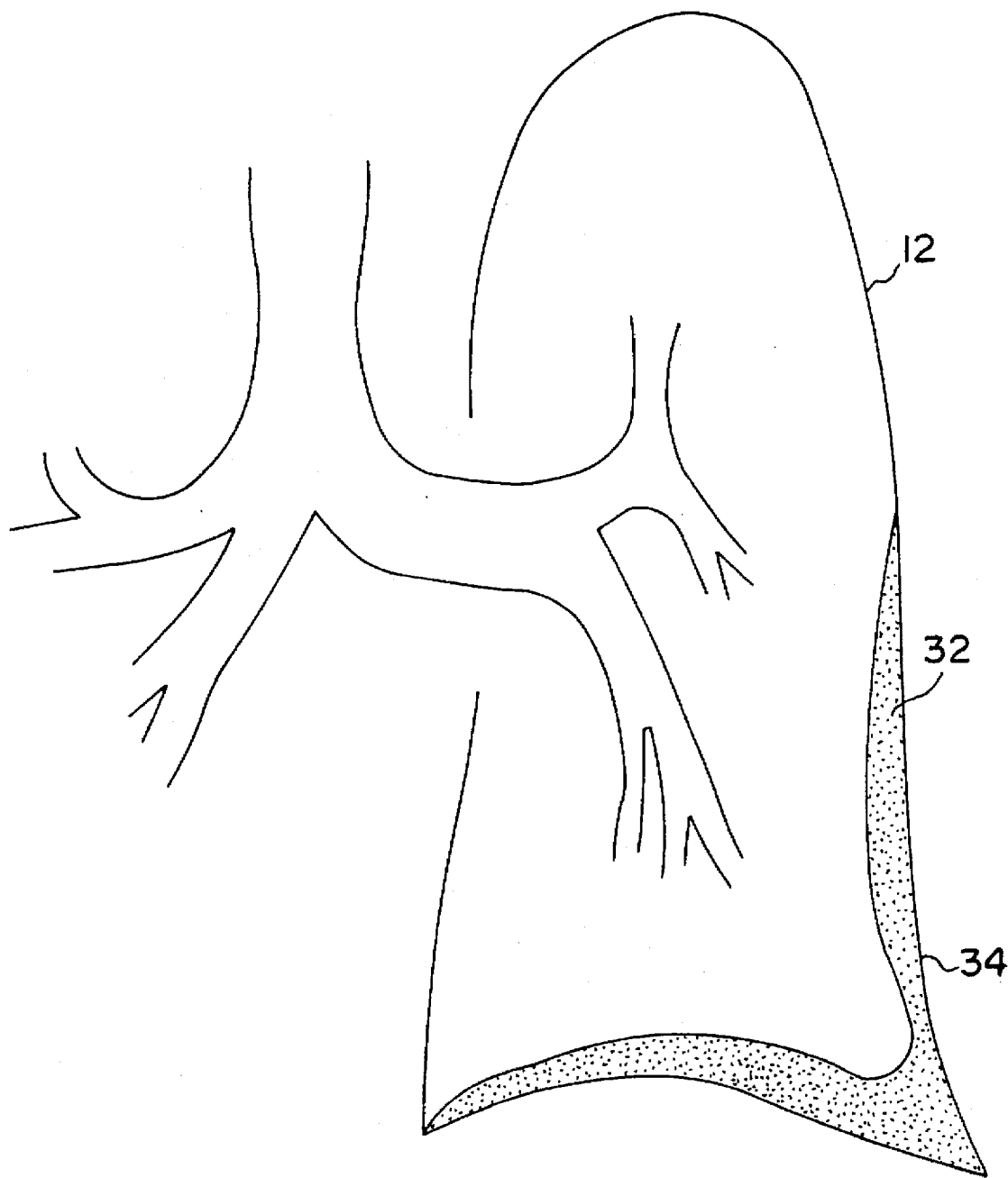
FIG. 2A illustrates a left lung with a pleural effusion.
Figure 2B:
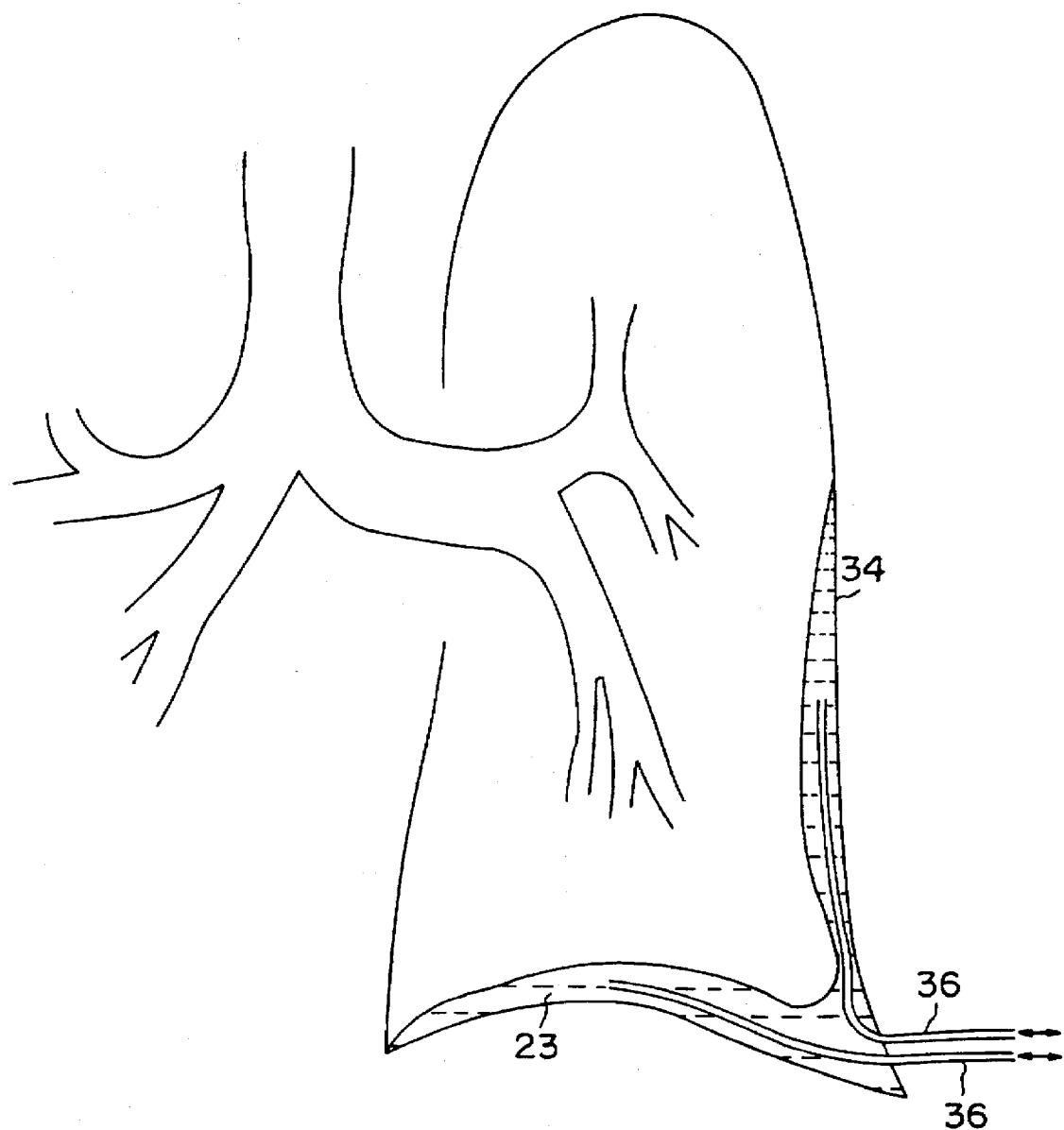
FIG. 2B shows the infusion of fluorochemical liquid according to the present invention.
Figure 2C:
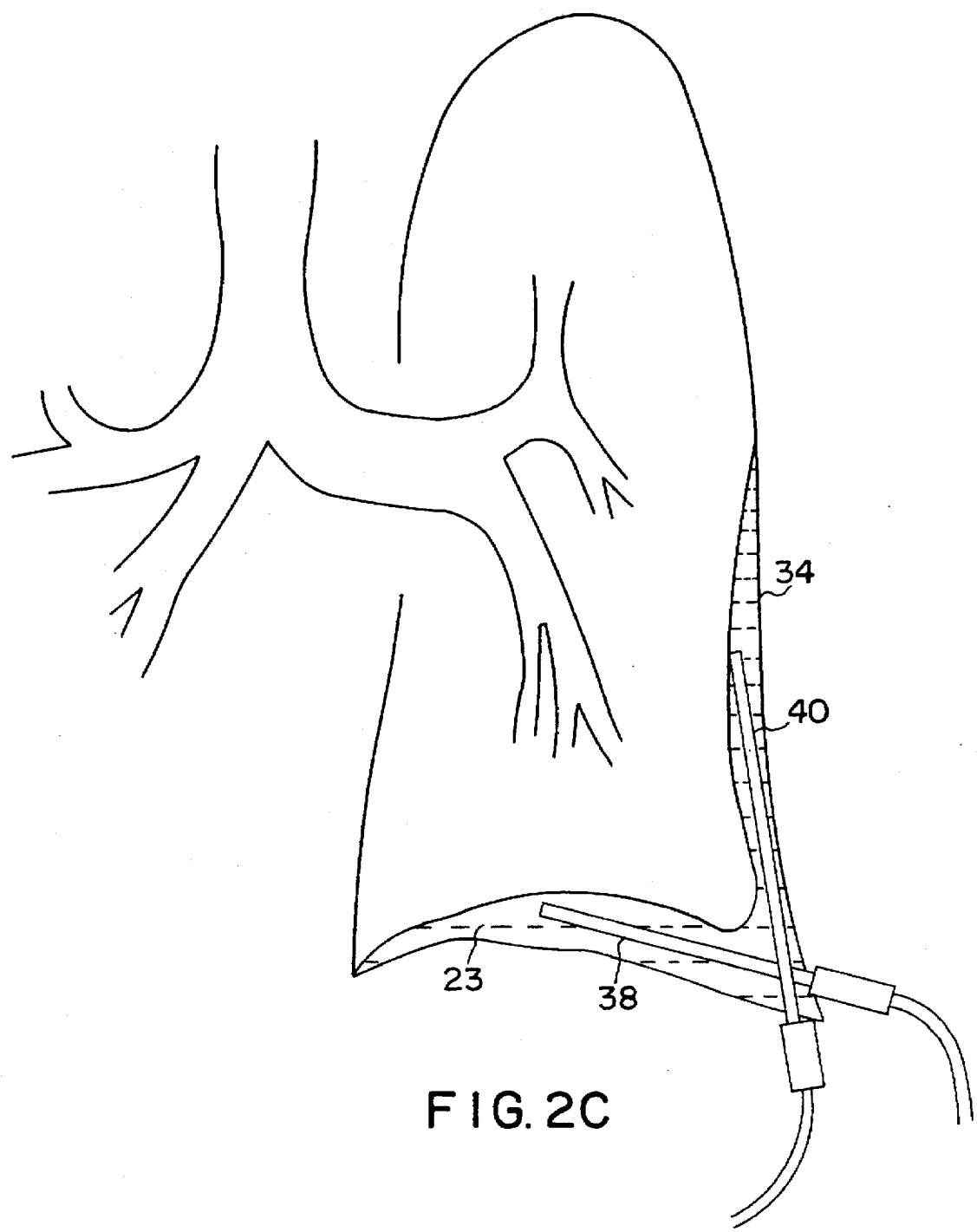
FIG. 2C illustrates the insertion of the cryogenic probes for producing ablation of the pleural effusion.

The PFC liquid may also be employed to physically alter the environment around the target lesion. By selecting a PFC liquid having a specific thermal conductivity and/or freezing point, the environment around the target lesion can be made either more or less conducive to promoting spread of the ice ball 30. If no PFC liquid is present in the lobe 22, or if the PFC liquid in the lobe 22 has the same thermal conductivity as the air in which it displaces, the ice ball 30 will develop in the normal manner. However, if the lobe 22 is filled with PFC liquid having a thermal conductivity higher than the air it displaces and/or a low freezing point, the PFC liquid will function to promote thermal conduction and thereby improve the freezing process. That is, the PFC liquid, which is preferably chosen to remain liquid at or below the freezing point of the surrounding tissue, circulates around causing the tissue to freeze. Hence, the ice ball 30 that develops is larger than the normally expected circumferential distance from the cryoprobe 26. Thus, a larger area can be frozen or reduced significantly in temperature than would otherwise be possible without the use of the PFC liquid. This embodiment makes possible cryogenic procedures in the lung that heretofore could not be performed with any degree of control (e.g., a lobectomy). Furthermore, PFC liquid with a high thermal conductivity and/or low freezing point can be instilled into the pleural space while performing this procedure to affect local thermal gradients and to extend freezing into recessed large surface areas. FIGS. 2A–2C provide a more detailed explanation of how to instill PFC liquid into the pleural space.

If the lobe 22 is filled with PFC liquid having a low thermal conductivity, the PFC liquid will inhibit the spread of the ice ball 30, and thus physically limit the area of freezing outside of the desired area. This is advantageous when goal is to freeze a small focal tumor and maximally spare adjacent normal lung tissue.

The PFC liquid may also be employed to physically alter the environment around the target lesion by controlling the temperature of the PFC liquid. For example, if the lobe 22 is filled with extremely cold PFC liquid, the ice ball 30 will develop more rapidly and will spread further outward from the cryoprobe 26.

Alternatively, warm PFC liquid will have the opposite effect. The warm PFC liquid will also protect cold-sensitive structures which are adjacent to the cryosurgical procedure. Although it is known in the art to place warmed liquid into and/or around target organs as a means for protecting adjacent cold-sensitive structures during cryogenic procedures (specifically, it is known to circulate a warmed saline solution through a urethral catheter to protect the urethra from thermal injury), the use of PFC liquid for this purpose has not, heretofore, been disclosed or suggested in the art.

The thermal conductivity of various fluorochemical liquids are readily available to those skilled in that art. Many of the preferred PFC liquids have thermal conductivities which fall within a range of between about 0.65 and about 0.70 milliwatts/cm/°C. For example, APF-100 (perfluorodimethylcyclohexane) has a thermal conductivity of about 0.65 milliwatts/cm/°C., while Caroxin-D ($C_{10}F_{22}O_2$) has a thermal conductivity of about 0.68 milliwatts/cm/°C. Biological tissue, on the other hand, has a thermal conductivity less than, but relatively close to the thermal conductivity of water, which is about 6.25 milliwatts/cm/°C. Air has a thermal conductivity of about 0.25 milliwatts/cm/°C.

The thermal freezing properties of the PFC liquids generally fall two groupings. The first grouping consists of PFC liquids which are prone to freezing during a cryogenic procedure. These PFC liquids have a freezing point which is near or above the temperatures generated during the cryogenic procedure. PFC's in this grouping are preferred in a cryogenic surgical procedure wherein it is desirable to freeze the PFC liquid so as to produce ablation of the lesion. One suitable PFC which falls within this grouping is APF-140 (perfluorodecalin) which freezes at about zero °C. Another suitable PFC is perfluorooctylbromide which freezes at about 4° C.

The second grouping of PFC liquids is not prone to freezing during a cryogenic procedure. That is, these PFC's have a relatively low freezing point, which is usually below the freezing point of living tissue. Accordingly, these PFC's are preferred in the cryogenic procedures where it is desirable to either extend the range of the cryogenic effect or, alternately, prevent the passage of the low temperatures developed during the procedure. Hence, the PFC will remain in its liquid form and, therefore, is capable of interdigitating into the interstices of the surrounding tissues. One preferred PFC is APF-100 (perfluorodimetheycyclohexane) which has a freezing point of about −69° C. This is typically well below the temperature generated during a cryogenic procedure. Hence, the PFC will remain liquid during the procedure.

Furthermore, techniques exist for determining the thermal conductivity of a fluorochemical liquid. Co-pending patent application entitled "Breathable Liquid Elimination Analysis", filed Jan. 17, 1995, Ser. No. 08/373,662, and incorporated herein by reference, discloses one method useful for determining the thermal conductivity of a fluorochemical liquid. The disclosed method is as follows.

Figure 13:
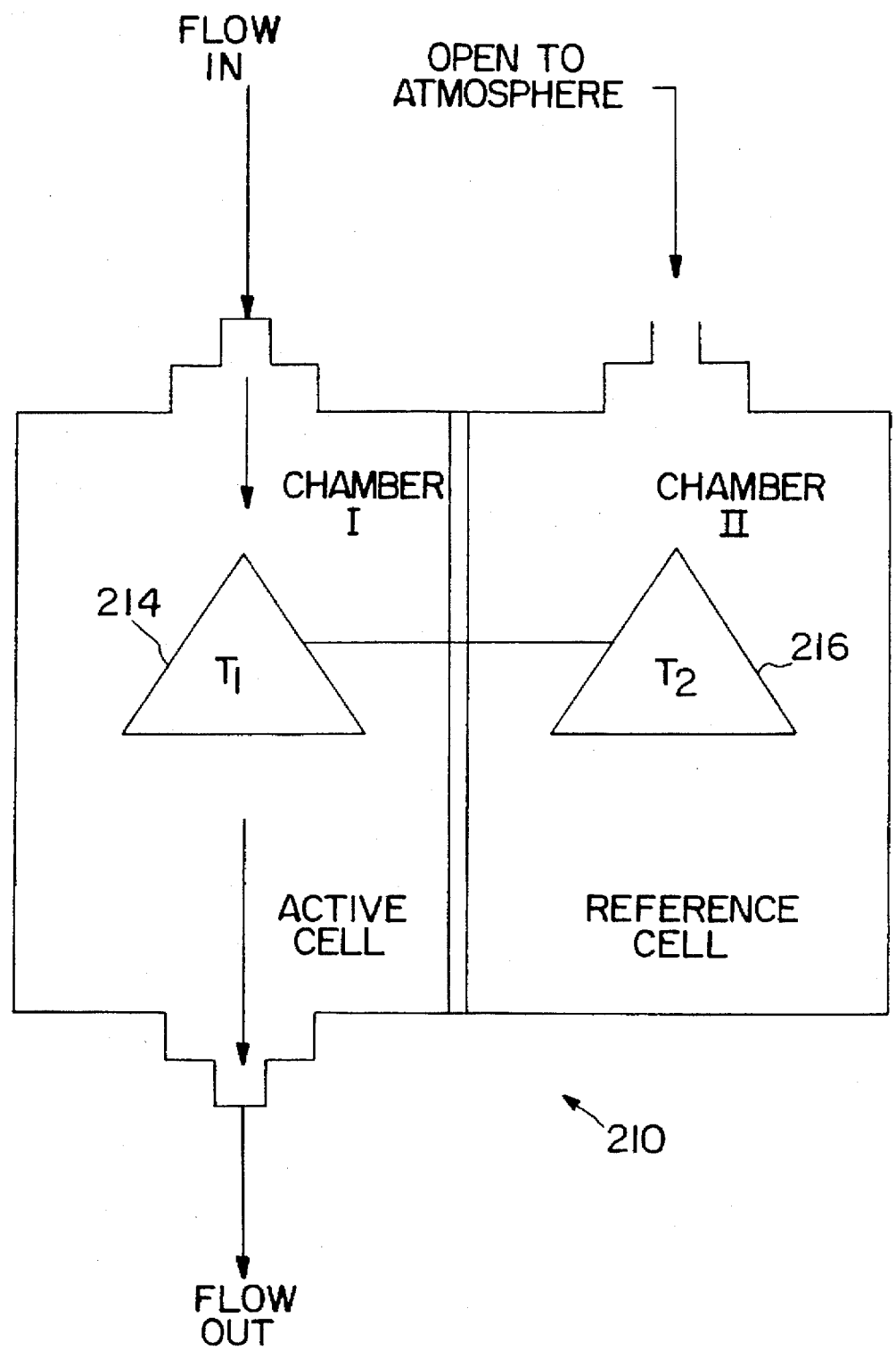
FIG. 13 schematically depicts an apparatus useful in determining the thermal conductivity of PFC liquids.

FIG. 13 is a schematic illustration of a portion of a thermal conductivity detector/analyzer 210 which can be employed to compare the thermal conductivities of perfluorochemicals with one another, as well as with the thermal conductivity of a known element, i.e., the standard. The principle of thermal conductivity, as applied to the thermal conductivity detector/analyzer employed herein, follows.

Thermal conductivity, K, is a measure of the heat flow across a surface per unit time, divided by the negative of the rate of change of temperature with distance in a direction perpendicular to the surface. Expressed another way, thermal conductivity is the time rate of transfer of heat by conduction, through a unit thickness, across a unit area and for a unit difference in temperature. It can thus be expressed as watts per meter-Kelvin. It can be measured as calories per second per square centimeter for a thickness of 1 cm and for a difference of temperature of 1 degree Celsius, or calories/(cm)(sec.)(°C.).

Heat flow through a substance is thus proportional to the area of the material and the resultant temperature change over a given distance. This resultant temperature change is dependent on the material's molecular properties. These include, but are not limited to specific heat, vapor pressure, viscosity, rate of flow of mass, charge, temperature and conduit diameter. For a given material at a given temperature, these other properties are constant and the flow of heat over a given distance can be represented as thermal conductivity, K.

The thermal conductivity detector/analyzer 210 in FIG. 13 utilizes the above principles to assess the thermal conductivity, K, of the PFCs. The detector/analyzer 210 utilizes a dual chamber design. PFC liquid flows at a known rate and at a given temperature through chamber I (the active cell). Chamber II (the reference cell) is open to atmosphere with no flow therethrough. Thermistors 214 ($T_1$) and 216 ($T_2$) are heated to a known temperature. The PFC liquid flow in Chamber I changes the temperature assessed by $T_1$, relative to $T_2$. This temperature gradient is converted to an analog voltage, processed by an A/D converter and represented as a digital output.

The detector/analyzer 210 is, typically, calibrated by using two standards which represent two known thermal conductivities. The thermal conductivities of the PFC liquids would be determined as a function or proportion of these standards. For example, it may be desirable to chose air and 100% oxygen to represent two bounds for comparison with the PFC liquids. Air, composed mostly of nitrogen, has a negligible thermal conductivity and thus registers an infinitesimally small temperature gradient between the thermistors 214 and 216. Thus, no voltage change occurs and the output is about 0.00 V. In contrast, the significantly higher thermal conductivity of oxygen produces a temperature gradient which results in an output of 1.58 V. These two outputs would be employed as the calibration standards.

The digital output signal from the detector/analyzer for each PFC liquid analyzed would be tabulated as a proportion of the thermal conductivities of the two chosen standards. The degree of temperature change is based on various thermodynamic properties intrinsic to the substance measured, and well known to those skilled in the art. Accordingly, based on the above test procedure, it is possible to determine the relative thermal conductivity of the various PFC liquids of interest.

The cryogenic procedure shown in FIGS. 1A–1D fills the lung with a fixed pool of PFC liquid. However, other filling techniques can be employed which allow for circulation and replenishment of PFC liquid. One benefit of circulating and replenishing PFC liquid (other than for permitting lung ventilation) is that the temperature of the PFC liquid can be carefully controlled to achieve the desired environment. One method of circulating PFC liquid is to employ two catheters 24, one to inject temperature controlled PFC liquid and one to remove PFC liquid. This method is described below with respect to FIG. 3. Other methods for filling the lung with PFC liquid include percutaneous transthoracic intraparenchymal injection and mebulized inhalation.

Fluorocarbon liquids such as PFC liquid transmit sound at a much faster rate than living tissue. The inventors have conducted testing which has shown that ice formations can be visualized with ultrasound equipment in PFC liquid environments. However, the speed differential between the sound traveling through the PFC liquid and the neighboring tissue distorts the resulting ultrasound image. Accordingly, it will be necessary to focus ultrasound probes specifically for lung applications to allow for these velocity differences. This can readily be accomplished through software and/or hardware modifications to the ultrasound equipment using existing technology which would focus the ultrasound probe when utilized in a PFC environment.

FIGS. 2A through 2C show an improved method for cryogenically treating localized pleural disease by employing a PFC liquid. Recurrent malignant and inflammatory pleural effusions are a difficult clinical problem which often require pleurodesis. Heretofore, cryosurgery of the pleura was not possible, except for very focal disease. The nature of cryoprobe freezing limits the geometry of the ice ball to elliptical volumes. However, PFC liquid can be employed as the freezing medium to extend the option of cryosurgery to widespread pleural processes. Mesothelioma and diffuse pleural metastases are treatable by instilling PFC liquid directly into the pleural space and cooling the liquid in contiguity with pleural surfaces. Ultrasound or other conventional imaging modalities are employed to identify and stage disease, as well as to monitor the freezing process. The PFC liquid enhances the imaging. Cryopleurodesis is similar to other cryosurgical procedures involving anatomic spaces, such as cryosurgical ablation of the endometrium of the uterus. The freezing is performed either by placing a cryoprobe into a pleural space filled with PFC liquid to freeze the space, wherein the PFC liquid will preferably have a high thermal conductivity and/or low freezing point to promote the freezing. This procedure can further enhance the freezing effect of the cryoprobe by using low temperature PFC liquid. To further promote the freezing process yet further, a cryoprobe having a broad, flat and thin profile can be employed. Such a probe can be approximated over a large area of the pleural surface.

FIG. 2A shows pleural effusion 32 in pleural space 34 interposed between visceral and parietal pleural layers the lung 12.

FIG. 2B shows the first step of the novel treatment method. Drainage catheters 36 are placed into the pleural space 34 to remove the fluid associated with the effusion. Then, PFC liquid 23 is infused into the pleural space 34.

FIG. 2C shows the next step of the novel treatment method. One or more cryoprobes 38, 40 are placed into the PFC liquid-filled pleural space 34. The cryoprobes 38, 40 cool the PFC liquid 23, which in turn, ablates lining cells and causes an inflammatory reaction which creates adhesions. That is, the PFC liquid over time causes sclerosis and obliteration of the pleural space, thereby preventing recurrent pleural collections. In malignant cases, this process ablates pleural tumors. As noted above (but not shown in FIG. 2C), ultrasound or other conventional imaging modalities are employed during this step to identify and stage disease, as well as to monitor the freezing process. An ice ball may develop in the immediate vicinity of the cryoprobe. However, the thermal injury to the pleural lining will be mediated predominantly by the PFC liquid that has been placed in that space and cooled to a suitable temperature. Preferably, a PFC liquid with a thermal conductivity higher than the air it displaced, a low freezing point and/or a low temperature is utilized such that it remains in liquid form when cooled, thereby maximizing the freezing contact with the pleural tissues. The PFC liquid is, preferably, chosen to remain liquid at the freezing point of the living tissue, i.e., at least below about zero degrees Celsius. When the treatment is completed, the PFC liquid 23 is drained from the pleural space 34.

The flat probes commonly utilized in the art could be employed in the above procedure when the pleural surfaces to be frozen are relatively small in size. For larger pleural surfaces, an inflatable probe, which could be filled with liquid nitrogen or similar type cryogenic agent, is preferable. The inflatable portion of the cryoprobe would be a non-elastic balloon that would conform to the surface to which it is applied. When used in a pleural space, the non-elastic balloon would be broad and flat in shape. The balloon would be formed from a material which could withstand the low temperatures and thermal gradients associated with cryogenic surgery. Those skilled in the art would be readily capable of choosing an appropriate material based on the cryogenic agent utilized. In the preferred embodiment a Mylar™ material (trademark of du Pont de Nemours & Co., Inc., Wilmington, Del.) is utilized to form the balloon. In use, the balloon is placed in the pleural space in a collapsed, deflated state. The pleural space is then filled with PFC. Next the balloon is filled with a suitable cryogenic agent, such as nitrogen, to lower the PFC in contiguity with the lung surface.

Figure 3:
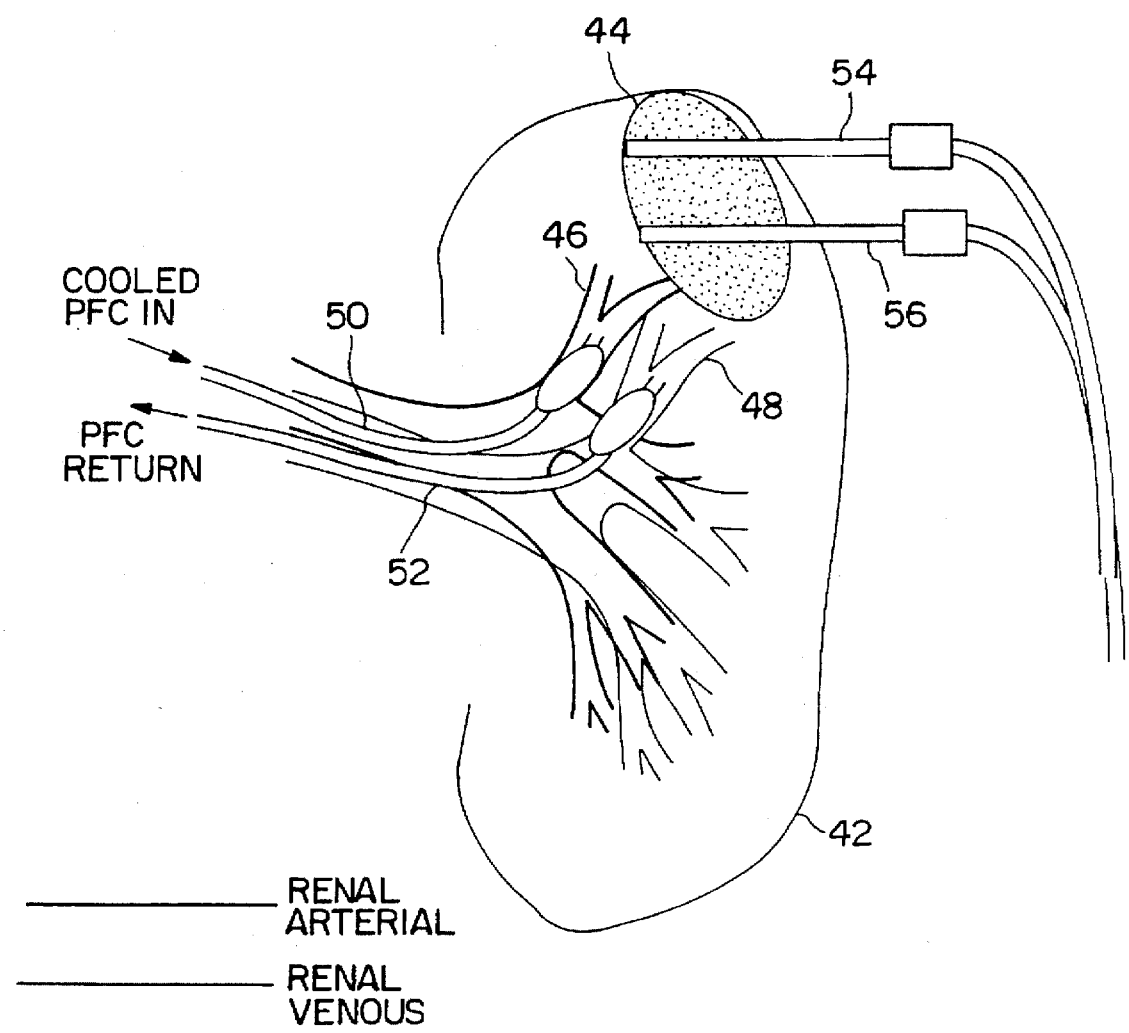
FIG. 3 illustrates a cryogenic procedure, according to the present invention, performed on a renal lesion.

PFC liquid-enhanced cryosurgery is also suitable for treating solid lesions, including vascular tumors. The target lesion is perfused by PFC liquid having appropriate thermal properties to allow good flow at low temperatures to assure patency (i.e., state of not being blocked or obstructed) of the vascular bed. One example of this novel procedure is shown in FIG. 3 which illustrates a method of cryogenically treating a renal lesion (e.g., renal cell carcinoma). The kidney is an end organ where perfusion of PFC liquid is easily isolated through the renal artery and vein.

FIG. 3 shows the environment for performing cryosurgery of a renal lesion. Kidney 42 has a renal tumor 44 therein. Renal feeding arteries 46 and renal draining veins 48 are in fluid communication with the tumor 44. Indwelling balloon catheters 50 and 52 are inserted into a segment of the artery 46 and vein 48, respectively. The balloons are then inflated to occlude both the artery 46 and vein 48. The tumor 44 is perfused with cooled PFC liquid through the arterial catheter 50 while warm PFC liquid is removed from the tumor 44 through the venous catheter 52. One or more cryoprobes 54, 56 are inserted into the tumor 44 and cryogenic fluid is circulated through the probe. Ultrasound or other conventional imaging modalities (not shown) are employed throughout this procedure to monitor the catheter and cryoprobe placement, as well as the overall freezing process. By selecting PFC liquid having a high thermal conductivity, a low temperature and/or a low freezing point, the PFC liquid in the tumor improves the cryosurgery by promoting better freezing by the cryoprobes (thereby allowing the ice balls to encompass a larger volume) and by maintaining vessel patency. Also, the PFC liquid inhibits coagulation of blood within tumor vasculature, allowing continued patency of these vessels during freezing and uninterrupted delivery of PFC to the tumor's vascular bed. When describing the delivery of the fluorochemical liquid, it is contemplated that the PFC can be delivered in or proximal to the lesion.

In FIG. 3, the perfusion process is achieved using angiographic (percutaneous) techniques. In other instances, surgical techniques may be used to perfuse the tumor 44, such as direct injection of PFC liquid into the tumor 44. In cystic tumors, direct instillation of PFC liquid is preferred since these tumors are relatively avascular.

PFC liquid-enhanced cryosurgery is also well-suited to the ablation of lesions in hollow structures. These include both hollow organs including the bladder and uterus, tubular structures such as ductal systems in the liver, breast, pancreas and the like, as well as hollow or cystic pathologic lesions such as cystic malignant and benign tumors and benign cysts of the liver, pancreas, breast, kidneys and abscesses in any part of the body. In each of these cases, hollow structures are drained of their contents and replaced with PFC liquid having the appropriate thermal characteristics, freezing points and starting temperatures.

Figure 4:
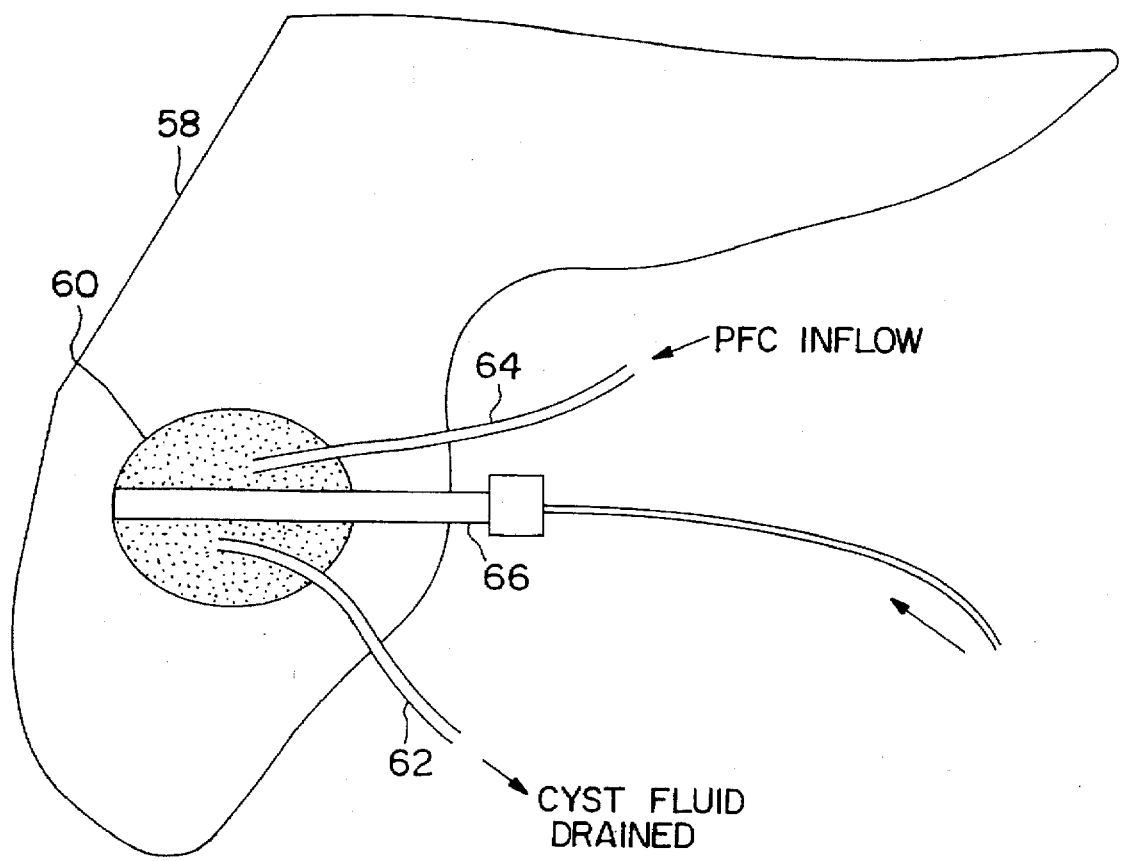
FIG. 4 shows the enhanced cryogenic surgery of a hepatic cyst in the liver according to the present invention.
Figure 5:
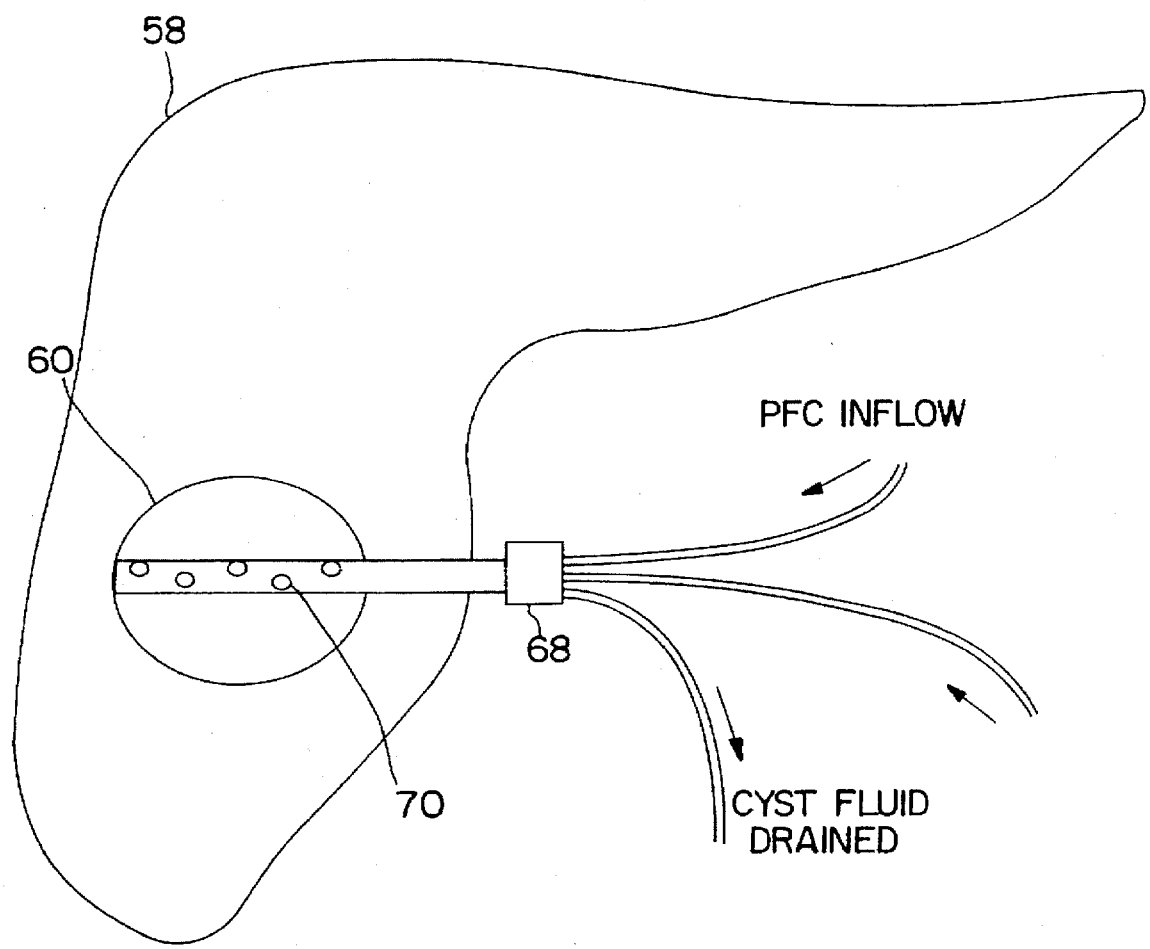
FIG. 5 illustrates the utilization of a novel cryoprobe in treating the hepatic cyst according to the present invention.

One example of this novel procedure is shown in FIGS. 4 and 5 which illustrate methods of cryogenically obliterating a hepatic cyst. Similar procedures may be employed for treating cysts of the pancreas, breast, kidney and the like, including a wide variety of benign, inflammatory, infectious and malignant cystic lesions. Such cysts can often cause significant clinical problems due to the pressure effects on contiguous structures caused by the size of the cyst or recurrent infection of the hemorrhage. These cysts are often percutaneously drained and sometimes require open surgery. Despite these maneuvers, many are unsuccessfully treated by conventional treatments.

FIG. 4 shows the environment for performing cryosurgery of a hepatic cyst. Liver 58 has a cyst 60 therein. Catheters 62 and 64 are inserted into the cyst. The catheter 62 drains the cyst 60 of its contents, while catheter 64 fills the cyst 60 with PFC liquid. Alternatively, a single catheter can be employed to both fill and drain the cyst 60. One or more cryoprobes 66 are inserted into the cyst 60 and cryogenic fluid is circulated through the probe. FIG. 4 shows one such cryoprobe 66. The low temperatures produced in the cyst 60 obliterates the cyst's endothelial lining cells which are responsible for secreting the fluid that causes them to enlarge. Ultrasound or other conventional imaging modalities (not shown) are employed throughout this procedure to monitor cryoprobe placement and the freezing process. By selecting PFC liquid having a high thermal conductivity, low temperature, and/or low freezing point, the PFC liquid in the cyst 60 improves the cryosurgery by promoting better freezing of the lesion by the cryoprobe 66. The physical amount of PFC liquid is selected to further improve the cryosurgery by infusing sufficient volumes of PFC liquid which minimize the size of the target, yet provide sufficient distension of the cyst to allow for obliteration of the cyst lining cells that are in contact with the PFC liquid.

FIG. 5 shows the environment for performing cryosurgery of a hepatic cyst using an alternative technique to fill and drain the cyst 60. In this embodiment, a modified cryoprobe 68 is inserted into cyst 60. Instead of draining and refilling the cyst 60 through a catheter, the cyst 60 is filled and drained through one or two fluid channels (not visible in this view) and a plurality of sideports 70 associated with the cryoprobe 68. This technique eliminates the steps of inserting separate filling and draining catheters.

In an alternate embodiment, the PFC liquid is chosen with a relatively high freezing point such that the PFC liquid will freeze within the cyst 60. Hence, the freezing of the PFC increases the effective area of ablation produced by the cryoprobe.

FIG. 6 shows the details of one version of the modified cryoprobe 68 for use in the procedure of FIG. 5. PFC liquid inflow catheter 72 feeds into sideports $70_1$, $70_2$ and $70_3$. Cyst fluid draining catheter 74 is in fluid connection with sideports $70_4$ and $70_5$. The sideports and catheters can be arranged in any suitable manner. A cryogenic fluid, such as liquid nitrogen, is circulated in a closed loop manner through a conduit (not shown) which extends the full length of the cryoprobe 68. The cryoprobe shown in FIG. 6 is preferably made from the same type of materials that are commonly used in existing cryoprobes.

PFC liquid-enhanced cryosurgery is also suitable for treating superficial lesions in hollow organs including transitional cell carcinoma of the bladder and ureters, lesions of the endometrial cavity, cystic lesions of bone, as well as diffuse processes of ductal systems. The ductal systems are treated by instilling PFC liquid into the duct and threading a modified cryoprobe into the duct. Infiltrative tumors and inflammatory disorders involving the ductal systems of the biliary system, breast, pancreas and salivary glands are also treatable by this novel method.

Figure 7:
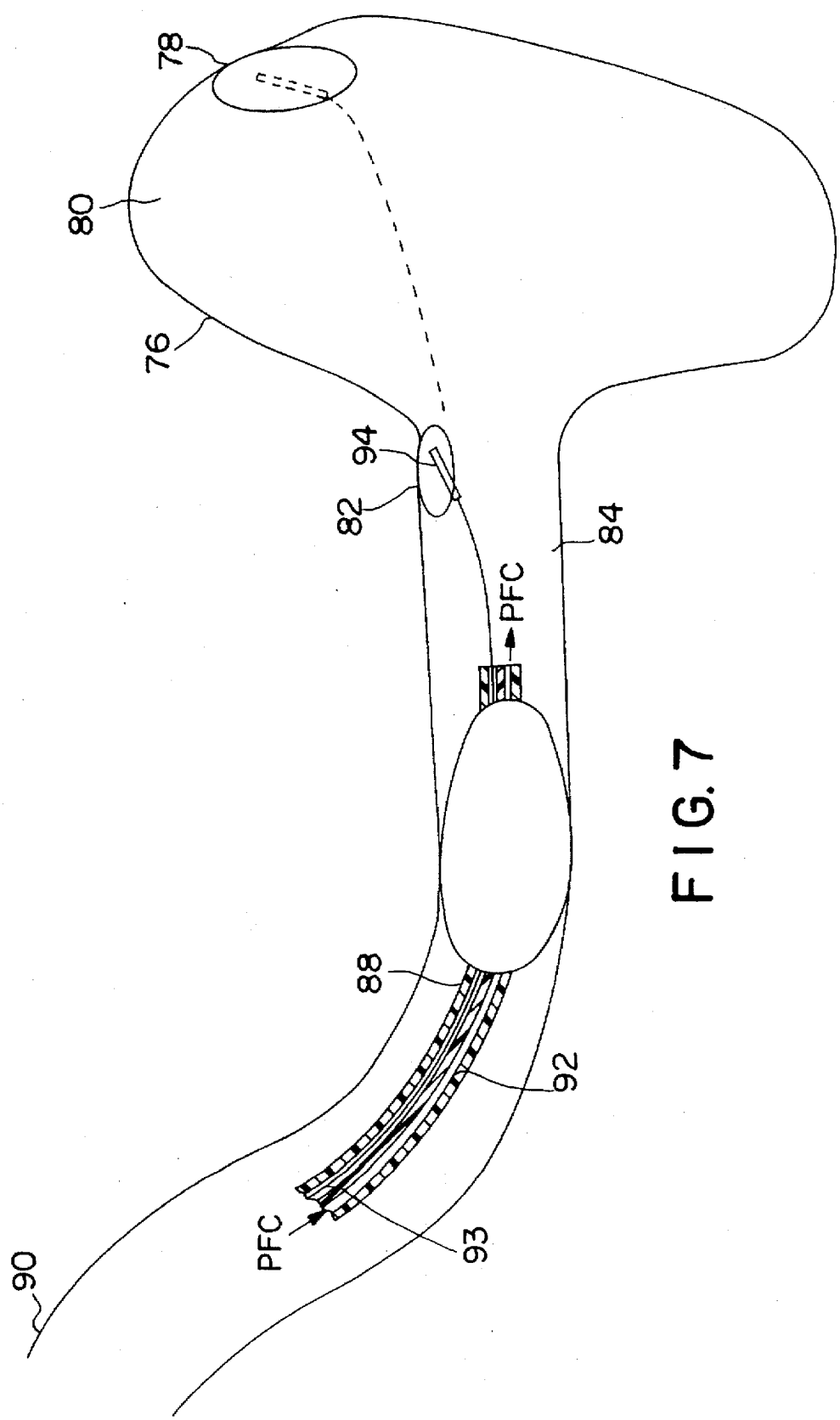
FIG. 7 illustrates the application of the present invention in a ductal hollow organ, such as the urinary bladder, with a combined catheter, fluorocarbon injector and cryoprobe device.

FIG. 7 shows the environment for performing cryosurgery of a lesion or tumor within a hollow organ or in the main duct of the organ. The urinary bladder is shown as an illustrative ductal hollow organ. Bladder 76 has a lesion 78 in bladder cavity 80 and another lesion 82 in main duct 84.

To cryogenically treat the lesion 78 or lesion 82, a balloon catheter 88 is inserted into urethra 90 to a selected location in the main duct 84. The balloon catheter 88 is, preferably, a double lumen catheter and includes first lumen 92 and second lumen 93. The balloon is inflated to occlude the duct 84. Then, the duct 84 and the bladder cavity 80 are instilled with PFC liquid through the catheter's first lumen 92. A small cryoprobe 94 is inserted through the catheter's second lumen 93 into either the lesion 82 in the main duct 84 (shown with solid lines), or into the lesion 78 in the bladder cavity 80 (shown with dashed lines). Cryogenic fluid is circulated through the cryoprobe 94 to freeze the lesion 78 or lesion 82, in the same manner as described in the previous procedures. Again, ultrasound or other conventional imaging modalities (not shown) are employed throughout this procedure to monitor cryoprobe placement and the freezing process. The double lumen catheter is constructed similar to a single lumen catheter, such as the Meduri Protected Lavage Catheter manufactured by Milrose, Inc., Waltham, Mass.

By selecting PFC liquid having a high thermal conductivity, low temperature, and/or low freezing point, the PFC liquid in the duct 84 and bladder cavity 80 improves the cryosurgery process by promoting better freezing by the cryoprobe 94. Alternatively, by selecting PFC liquid having a low thermal conductivity and/or high temperature the PFC liquid will inhibit the spread of the ice ball during the freezing process, and thus physically limit the area of freezing outside of the desired area (i.e., the area immediately adjacent to where the cryoprobe 94 is placed). This will help to spare adjacent normal tissue.

The procedure in FIG. 7 is also applicable to treating lesions in glandular ducts.

The general cryosurgical technique for treating a lesion or tumor within a hollow organ or in the main duct of the organ is also applicable to treating arteriosclerosis, especially atherosclerosis. It is a well-known fact that large vessels tolerate freezing well. Experience in hepatic cryosurgery has demonstrated that larger hepatic veins and arteries remain patent (i.e., open) even when placed in near direct contact with cryoprobes at −180 degrees Celsius. The novel PFC liquid-enhanced treatment of atherosclerotic disease ablates focal lesions by freezing them within a PFC liquid filled vessel segment. The segment is isolated by balloon catheters through which a modified, thin cryoprobe is placed.

Figure 8:
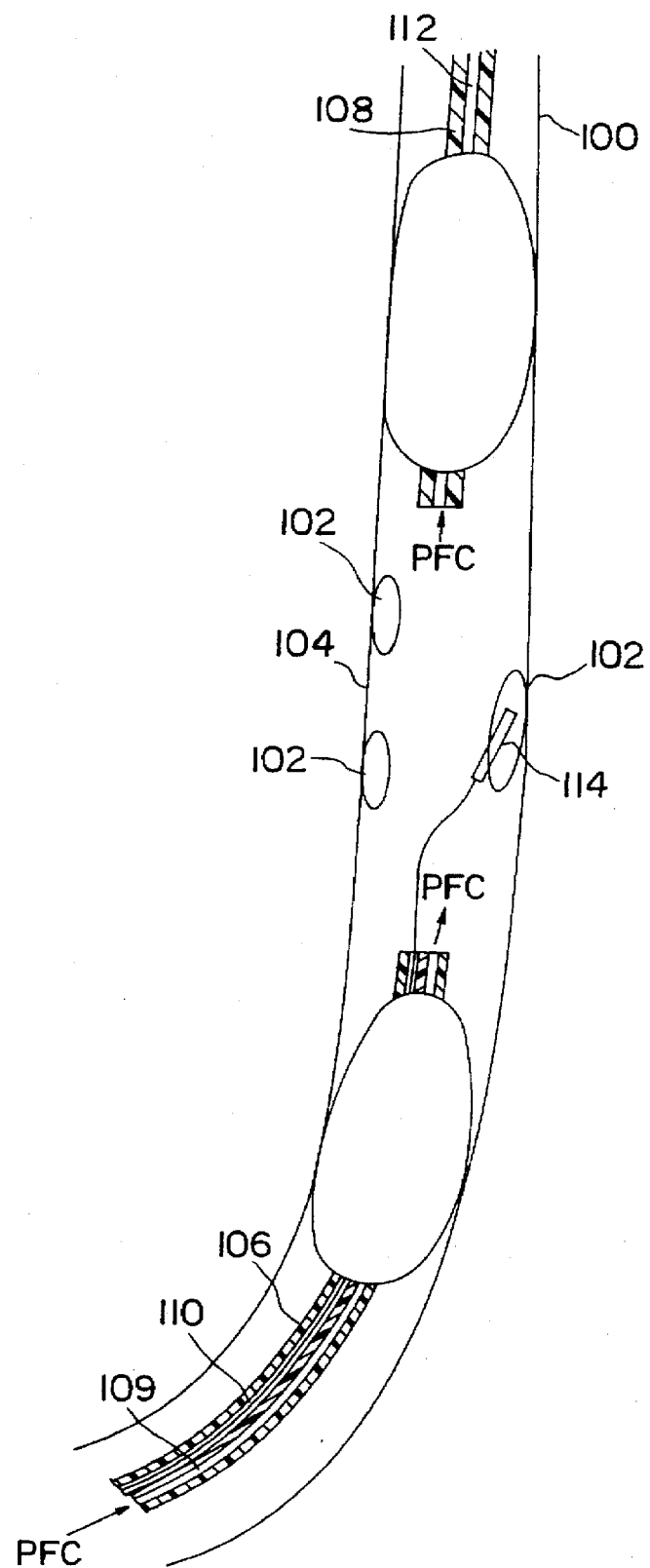
FIG. 8 shows a cryogenic procedure performed, according to the present invention, on an artery with atherosclerosis.

FIG. 8 shows the environment for performing cryosurgery to treat lesions associated with atherosclerosis. Artery 100 has one or more lesions 102 in artery portion 104. The lesions may be either localized or may cover entire sections of the artery portion 104. To cryogenically treat the lesions 102, balloon catheters 106 and 108 are placed at respective ends of the artery portion 104 and inflated to block off the ends. The balloon catheter 106, in this embodiment, is a double lumen catheter and includes first lumen 109 and second lumen 110. The balloon catheter 108 includes an optional single lumen 112. The artery portion 104 is instilled with PFC liquid through the first lumen 109 of the catheter 106. A small cryoprobe 114 is then inserted through the second lumen 110 of the catheter 106 into the artery portion 104. In order to function properly, the thin cryoprobe would have to be flexible in order to be channeled through the lumen. A cryoprobe 114 made from a material, such as Mylar™, would be sufficiently flexible yet capable of withstanding the low temperatures involved in a cryogenic procedure.

If there are a small number of well-defined lesions 102, the cryoprobe 114 is inserted directly into the lesion 102, as shown in FIG. 8, and cryogenic fluid fed thereto. However, if the lesions 102 are so large or numerous in number that they effectively coat the inside of the artery wall, the cryoprobe 114 is merely positioned in the lumen of the artery portion 104. Cryogenic fluid is circulated through the cryoprobe 114 to freeze the lesions 102, in the same manner as described in the previous procedures. Again, ultrasound or other conventional imaging modalities (not shown) are employed throughout this procedure to monitor cryoprobe placement and the freezing process.

If it is desired to circulate low temperature PFC liquid through the artery portion 104 to further promote freezing, the optional lumen 112 of the balloon catheter 108 functions as the return path for warm PFC liquid.

By selecting PFC liquid having a high thermal conductivity, low temperature, and/or low freezing point, the PFC liquid in the artery portion 104 improves the cryosurgery by promoting better freezing by the cryoprobe 114. Alternately, by selecting PFC liquid having a low thermal conductivity and/or high temperature, the PFC liquid will inhibit the spread of the ice ball during the freezing process, and thus physically limit the area of freezing outside of the desired area (i.e., the area immediately adjacent to where the cryoprobe 114 is placed). This will help to spare adjacent normal tissue.

Figure 9:
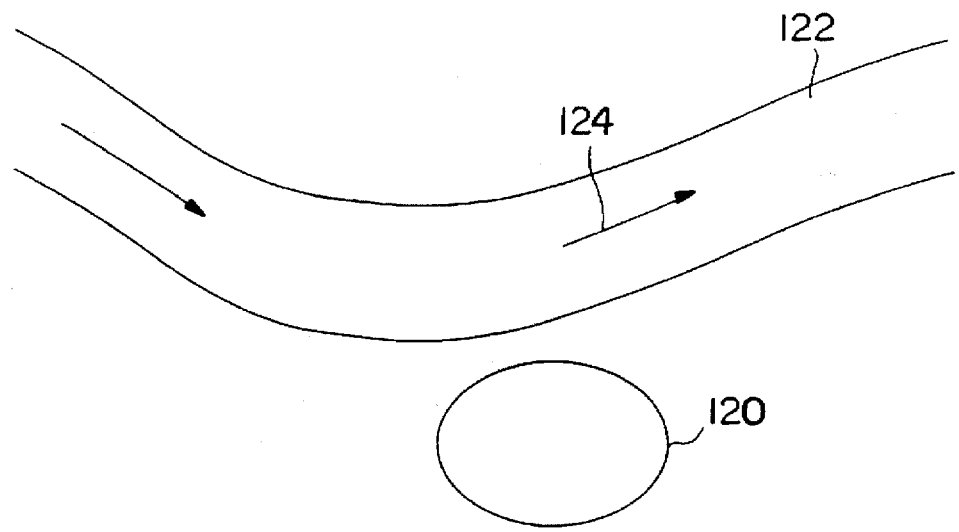
FIG. 9 illustrates a tumor located adjacent to a large blood vessel.

Referring now to FIG. 9, one current problem in conventional cryosurgery is the high failure rate at large vessel interfaces. That is, tumor cells 120 adjacent to large vessels 122, such as the aorta and inferior vena cava, are protected by the large volumes of blood 124 flowing therein. It is not currently possible to occlude these vessels transiently during cryosurgery, since this would result in vascular injury. Similarly, lowering the temperature of the tumor region by replacing the blood with cold fluorocarbon liquid places these vessels at risk. One solution to this problem is shown in FIGS. 10A and 10B and involves directly injecting a mediating fluid, such as PFC liquid, into the tumor region.

Figure 10A:
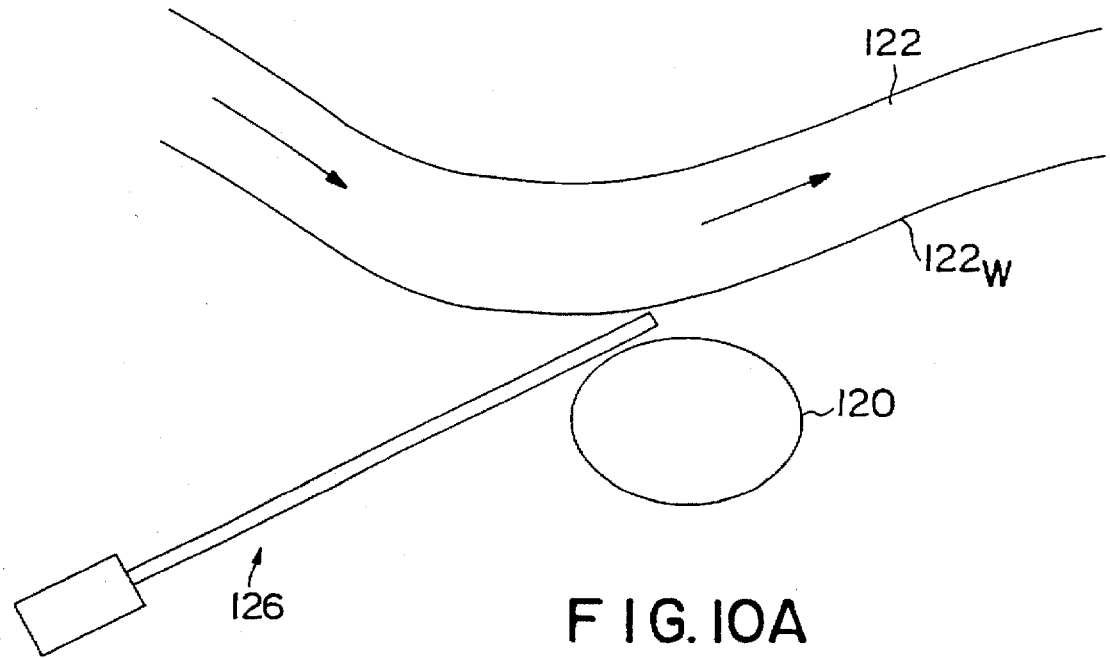
FIG. 10A shows the placement of a fluorocarbon liquid applicator between the tumor and the large vessel according to the present invention.
Figure 10B:
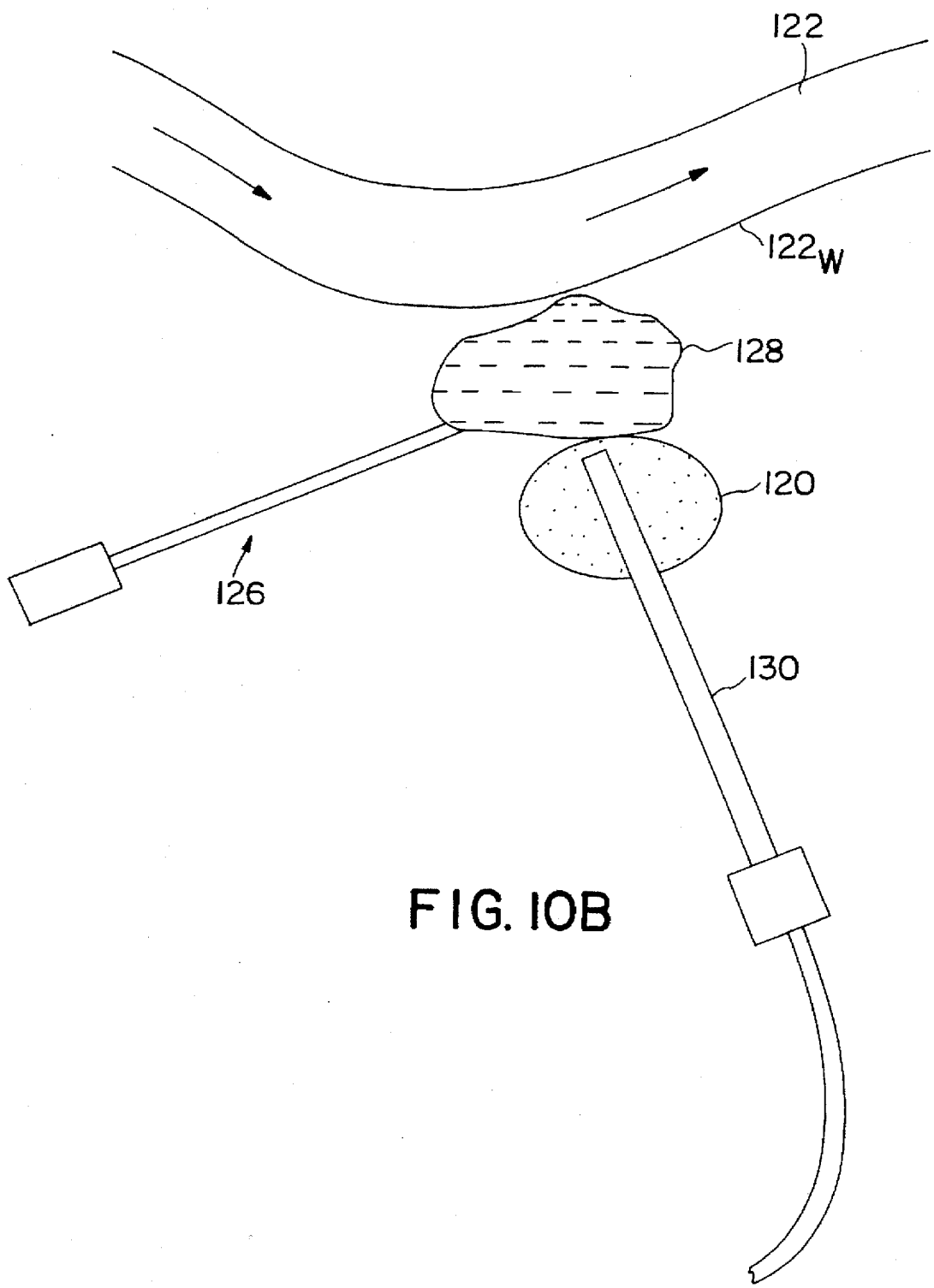
FIG. 10B show the formation of a puddle of fluorocarbon liquid for separating the tumor from the large vessel, and the insertion of the cryoprobe for conducting cryogenic surgery.

FIG. 10A shows a tumor 120 positioned in close proximity to the external wall $122_W$ of the large vessel 122. As stated above, cryosurgery was typically not performed in this region due to the likely vessel damage that would result from the cold environment developed during the procedure. The novel cryogenic technique illustrated involves placing a suitable means 126 for injecting PFC fluid, such as a needle, into the parenchyma between the tumor 120 and the vessel 122. Ultrasound techniques could be utilized to assist in properly locating the needle 126 between the tumor 120 and the vessel 122. PFC liquid is then injected into the parenchyma and, since the PFC liquid will not readily soak into the tumor 120 or vessel 122, a puddle 128 will form, as shown in FIG. 10B. The puddle 128 of PFC liquid provides two unique functions. Firstly, the puddle 128 separates the tumor 120 from the vessel wall $122_W$, thus providing a safer environment in which to perform the cryogenic procedure. Secondly, properly chosen PFC liquid acts as a thermal insulator, preventing the low temperatures developed in the tumor 120 during the cryogenic process from transferring to the vessel 122. In the preferred embodiment, the PFC liquid is chosen with a low thermal conductivity and/or high temperature. A cryoprobe 130 is subsequently inserted into the tumor 120 to produce ablation.

Figure 11:
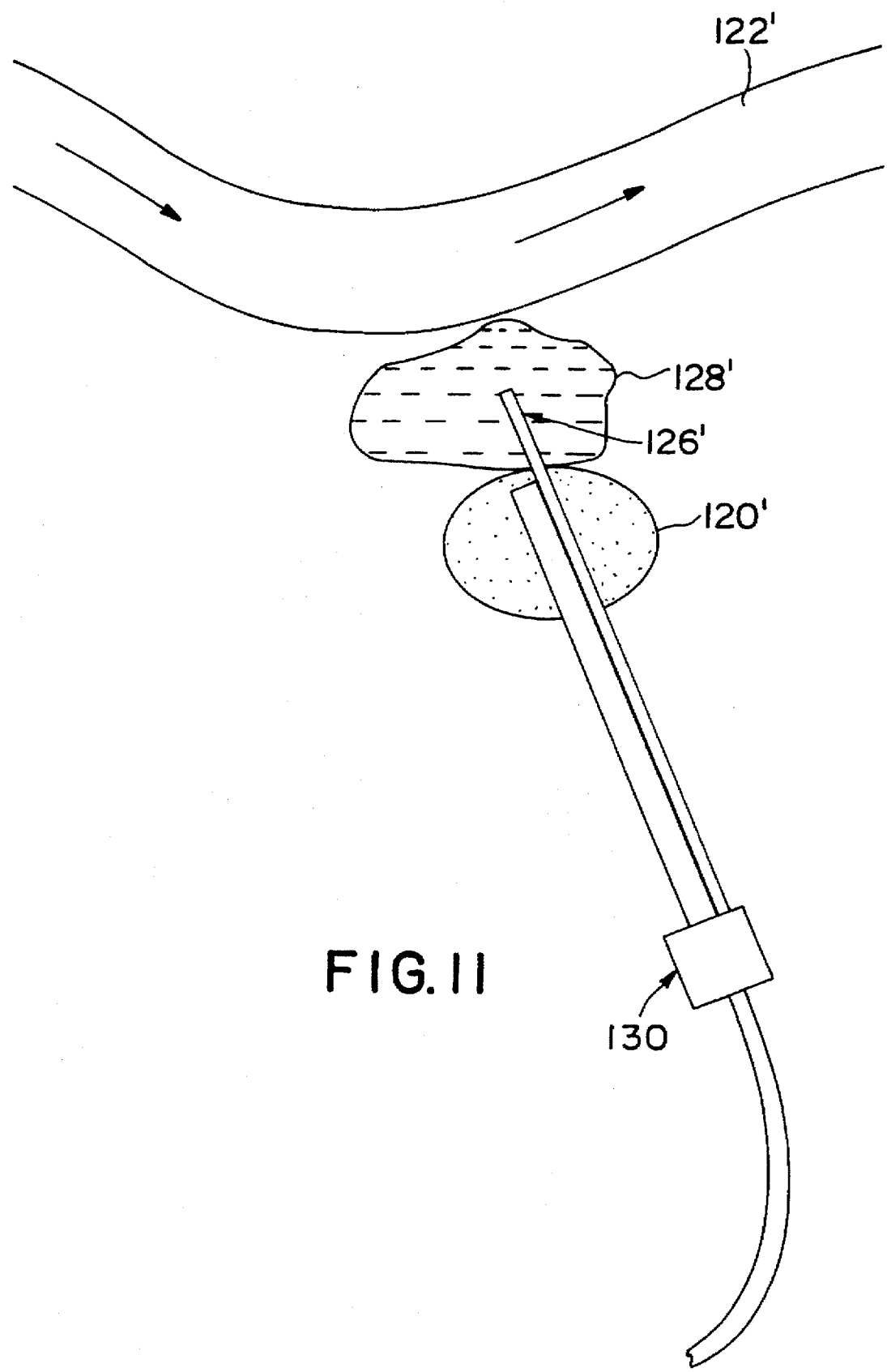
FIG. 11 illustrates an alternate embodiment of the cryogenic procedure shown in FIGS. 10A and 10B utilizing a novel cryogenic probe.

An alternate embodiment of the above novel procedure is shown in FIG. 11. A uniquely configured cryoprobe 130' is inserted into the tumor 120'. The cryoprobe 130' has integrated therewith a suitable means 126' for injecting a PFC liquid, such as a needle. The needle 126' extends past the tip of the cryoprobe 130' so as to provide a suitable puddle 128' of PFC liquid on the opposite side of the tumor 120'. This embodiment is especially useful in situations where access to the vessel 122' is prevented by the location of the tumor 120'. Accordingly, the only way to form a puddle 128' of PFC liquid is by passing the needle 126' through the tumor 120'. In order to provide for various tumor 120' thicknesses, the needle 126' would be designed so as to be extendable from the cryoprobe (e.g., telescope outward).

Figure 12A:
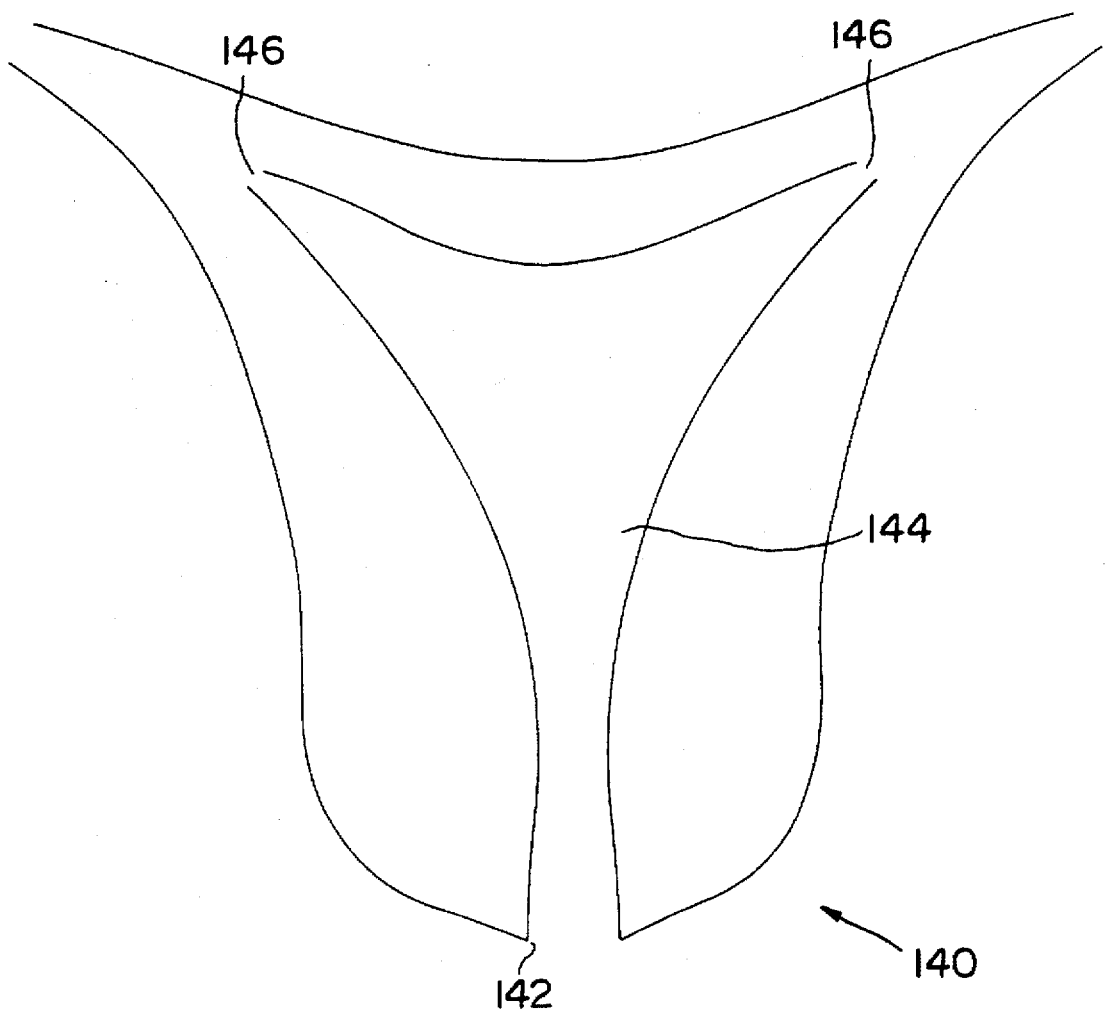
FIGS. 12A and 12B illustrate the present invention when utilized to ablate the endometrial lining of a uterus.
Figure 12B:
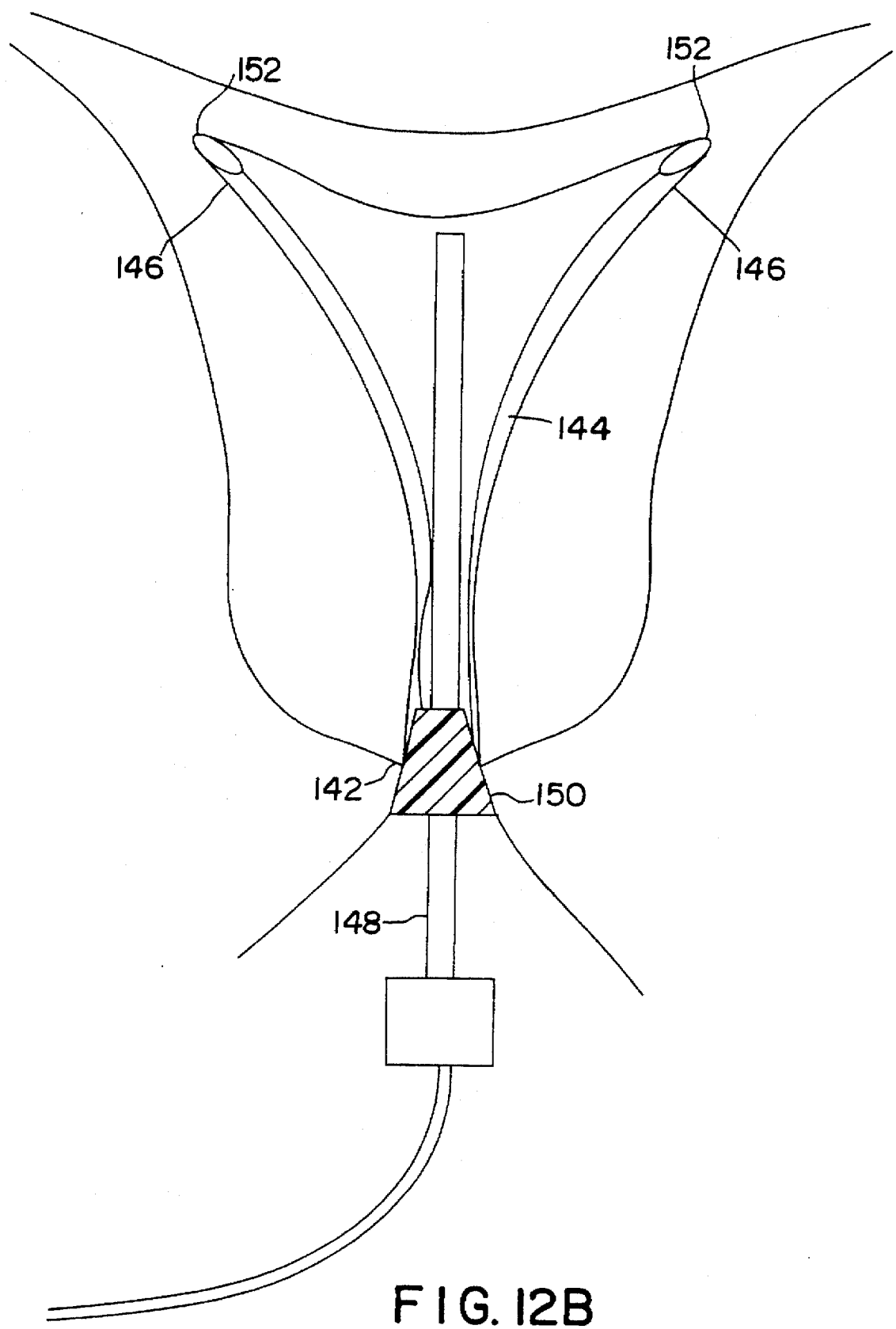
Figure 12C:
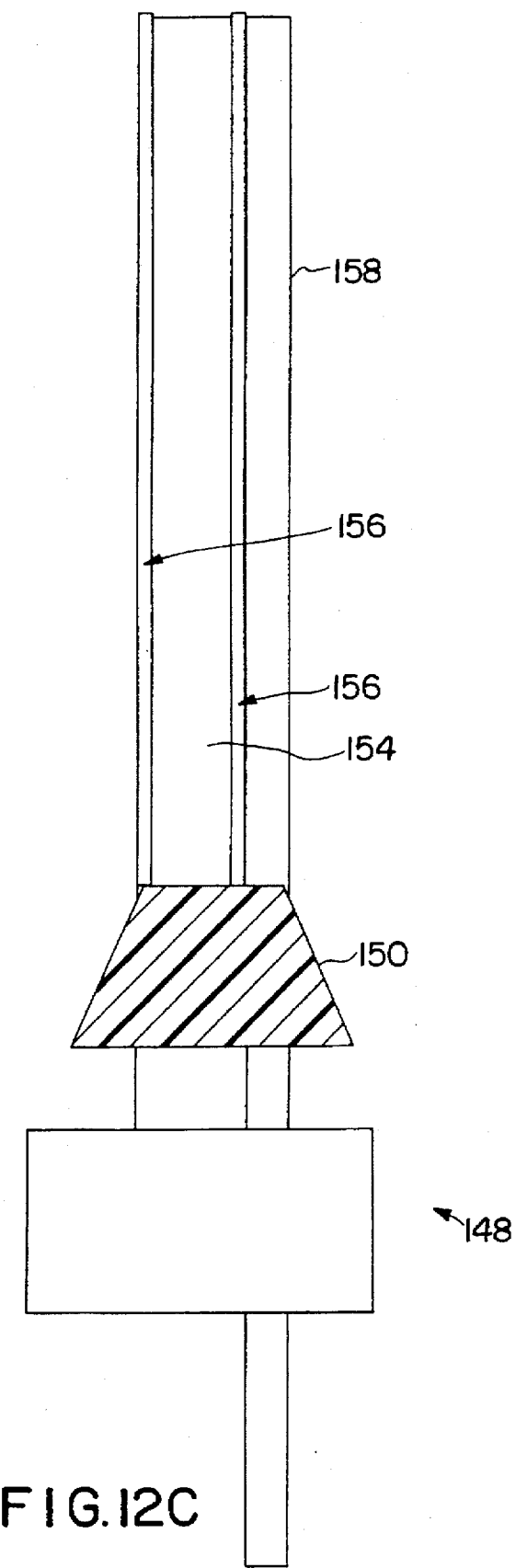
FIG. 12C shows a novel cryoprobe embodiment for use in the endometrial ablation procedure illustrated in FIGS. 12A and 12B.

FIGS. 12A through 12C illustrate the utilization of the present invention in an endometrial cryoablation procedure. Dysfunctional uterine bleeding is a common medical problem accounting for a significant number of medical procedures including D&C, hysterectomy and laser surgery. Cryosurgical ablation of the endometrial lining has been tried in at least one foreign study (Mrcog, R. P. and Majid, S., "Endometrial cryoablation using 0.9% saline as a uterine distension medium: a feasibility study", *Minimally Invasive Therapy*, 1992; pp. 283–286). Ultrasound was not utilized in the procedure. The study indicated that incomplete obliteration of the cornua (edges) of the uterine cavity may occur. This was so even though distension with saline was utilized.

The novel technique presented utilizes PFC liquid as a distension medium. The preferred PFC liquid has a high thermal conductivity and/or low freezing point so that complete cryoablation can be achieved, even in small recesses which might not otherwise reach sufficiently low temperatures. The uterus 140 anatomy is depicted in FIG. 12A and includes a cervical os 142, a endometrial cavity 144, and a uterine cornua 146.

The procedure, illustrated in FIG. 12B, involves placing a cryoprobe 148 through the cervical os 142 and occluding the os with either a balloon or wedge-shaped occluder 150. Blunt tipped or balloon occluders 152 are placed in the cornua 146 (i.e., the orifices of the fallopian tubes) to prevent leakage of PFC liquid into the fallopian tubes. This is achieved by passing the occluders 152 through channels formed in the cryoprobe 148 or alongside the cryoprobe 148, as shown in FIG. 12C. Ultrasound techniques are utilized to assist in directing the placement of the occluders 152 in the cornua 146. After the cornua 146 are occluded, the uterine or endometrial cavity 144 is filled with PFC liquid via channels in the cryoprobe 148. Preferably the PFC liquid has a low freezing point relative to the surrounding biological tissue. The PFC will, accordingly, remain liquid during the cryogenic procedure and interdigitate into the interstices of the cornua. The cryoprobe 148 is then turned on, causing some iceball formation but, more importantly, lowering the temperature of the PFC to freeze the endometrial lining into the cornua recesses. Monitoring of the procedure can be accomplished through the use of abdominal and/or endovaginal ultrasound, fluoroscopy or magnetic resonance.

Referring to FIG. 12C, one embodiment of the cryoprobe 148 utilized in the above procedure is illustrated. The cryoprobe 148 includes a flow circuit 154 for the cryogenic agent (e.g., liquid nitrogen) with two side channels 156 for transferring the cornua occluders 152. A PFC channel 158 may be integral with or separately attached to the cryoprobe 148. The PFC channel 158 may also be constructed so as to be capable of telescoping outward from the cryoprobe 148. A cervical os occluder 150 is positioned around the channels of the cryoprobe 148 so as to be capable of properly sealing the cervical os 142 when the cryoprobe 148 is positioned within the cervical cavity 144. As stated above, the cervical os occluder 150 may be formed as a wedge or, alternately, as a inflatable balloon. The occluder 150 may also be configured so as to be slidable along the channels of the cryoprobe 148 to provide further adjustment. Those skilled in the art would readily appreciate the various embodiments of the cryoprobe that may be practiced within the scope of this invention.

It is also envisioned that the present invention may be utilized in certain procedures where it is desirable to first liquify a solid tumor by conventional techniques before filling the lesion with the PFC liquid. The conventional freezing of a tumor in a cryogenic procedure, without the use of PFC, liquifies much of the tumor leaving necrotic (i.e., dead) tissue. However, tumors have an extensive blood vessel network associated with them. These blood vessels provide a substantial supply of blood which interferes with the freezing process, thereby reducing the effectiveness of the cryogenic procedure.

Accordingly, in order to enhance the standard cryogenic procedure, after the tumor is liquified, the liquid material is evacuated, such as through a drainage catheter. This leaves a void in the previous location of the solid tumor. The void is then filled with a PFC liquid, preferably chosen with a high conductivity, low temperature and/or low freezing point. The cryoprobe will reduce the temperature of the PFC so as to obliterate the remaining vascular bed which serviced the tumor with the blood supply. The liquid state of the PFC permits it to interdigitate through the remaining tissue to better ensure that the remnants of the tumor are killed.

Additionally, since the cystic (liquid) tumor is more sensitive to PFC liquid than a solid tumor, the PFC will have an enhanced effect on it. Accordingly, there is a significant benefit to liquifying the tumor prior to the PFC/cryoprobe procedure. FIGS. 4 and 5 generally illustrate this novel procedure. However, the PFC flow in catheter 64 is delayed until substantially all the liquid from the tumor is drained out of catheter 62. Alternately, a single catheter may be used which first drains the liquified tumor then fills the void with the PFC liquid.

In many of the embodiments of the invention disclosed above, it is preferable that the physical characteristics of the fluorochemical be selected such that it remains in a liquid state at sufficiently low temperatures, e.g., below zero degrees Celsius. However, as discussed above, the PFC can also be chosen with physical characteristics that results in freezing of the PFC during the cryogenic procedure, thereby enhancing the size of the ice ball formed during the cryogenic procedure.

U.S. Pat. No. 5,158,536, incorporated herein by reference, discloses various configurations and materials for manufacturing balloon catheters and cryoprobes which could be used in the present invention.

In another embodiment of the invention, a cystic lesion is removed by circulating cooled PFC liquid in and/or around the lesion without the need for a cryogenic probe. In this non-cryoprobe embodiment, a PFC liquid is utilized which remains in a liquid state at a temperature which is below the freezing temperature of living tissue. During the course of the procedure, the PFC liquid is cooled to a temperature below the freezing point of living tissue. The cooled PFC, which is still in its liquid state, is directly infused into the cystic lesion. Exposing the walls of the cyst to the low temperature of the PFC liquid causes distention and ablation of the cyst without the need for a cryoprobe. The cooled PFC in this novel embodiment also enhances the imaging of the cystic lesion.

One procedure for which the above embodiment is particularly useful is an endometrial cryoablation procedure. This procedure is similar to the embodiment illustrated in FIGS. 12A–12C, however, no cryoprobe is utilized. FIG. 14 illustrates this embodiment in more detail. The uterus configuration has been discussed above. As discussed above with respect to FIGS. 12A–12C, a ballon or wedge shaped occluder 162 is utilized to block the cervical os 142, and occluders 164 are used to block the cornua which lead to the fallopian tubes. A PFC catheter 160 is utilized to direct the PFC liquid into the endometrial cavity 144. The catheter 160 is inserted into the uterus, preferably through the cervical os 142. The catheter 160 includes a central shaft or tube 166 which provides a conduit for the PFC liquid to flow through. If, as is preferred, a circulation of PFC liquid into and out of the uterus is desired, the central tub 160 includes an input channel $166_A$ and an output channel $166_B$. The input channel supplies the cooled PFC liquid to the uterus. The output channel returns warmed PFC liquid to an external source. The materials from which the catheter 160 is manufactured must be capable of withstanding the temperatures which are likely to exist during this procedure. Suitable materials and/or catheters exist and are well known to those skilled in the art.

A pump 168 or similar device is utilized to circulate the PFC liquid into the uterus. In order to maintain the PFC liquid at a temperature below the freezing point of living tissue, a heat exchanger 170 is incorporated. The heat exchanger lowers the temperature of the PFC liquid by removing the heat energy in the liquid. Suitable heat exchanging devices are well known in the art and, accordingly, no further discussion is necessary.

In the above embodiments, occluders and have been utilized to prevent the PFC liquid from entering unwanted canals. However, it is also possible to, instead, utilize PFC liquid which has high viscosity characteristics. The high viscosity inhibits the travel of the PFC liquid while still providing the localized freezing/warming desired. As a result, occluders may be eliminated in certain procedures. For example, the use of high viscosity PFC liquid during an endometrial cryoablation procedure may eliminate the need for the placement of occluders in the cornua. The viscous PFC can be poured into the uterus and will assume the cavity shape. The high viscosity of the liquid prevents or minimizes the likelihood that the PFC will flow into the fallopian tubes. Another example where the use of high viscosity PFC has beneficial results is in the novel procedure described above with resect to FIG. 11. In that embodiment, the PFC liquid was placed between the cystic lesion and a blood vessel. Warmed PFC was utilized to inhibit the transmission of the freezing cryoprobe temperature to the blood vessel. The utilization of high viscosity PFC enhances this procedure inasmuch as the PFC will more readily "puddle" between the blood vessel and the tumor.

The above disclosed non-cryoprobe/cooled PFC liquid procedure can be used in any surgical procedure wherein it is desirable to ablate tissue in a cavity, space or potential space in a body. For example, besides the uterus, the procedure is useful in the bladder, bowel, sinuses, ear, CSF space, ductal systems of the liver and breast, lung, pleural space, cysts in any organ, cystic tumors, necrotic tumors, and abscesses. It can also be utilized in spaces that have been created iatrogenically such as areas of prior surgery, previously frozen lesions that have undergone central liquefaction and necrosis, previously radiated lesions with subsequent central necrosis and cyst formation, etc.

One type of commonly produced PFC liquid which has suitably high viscosity is APF-260. Its viscosity at 25° C. is 40.55 cSt, which is about 40 times more viscous than APF-100 (1.11 cSt at 25° C.). The freezing point for APF-260 is approximately −40° C. APF-215A (perfluoro isopropyl methyl decalin) and APF-215B (perfluoro sec-butyl decalin) are also highly viscous perfluorochemical liquids and have a very low freezing point which makes them particularly useful in the non-cryoprobe embodiment. Their respective viscosities are 7.57 cSt and 7.20 cSt and freezing points are −67° C. and −69° C. The above PFC liquids are provided as examples and are, by no means, intended to be limiting. In some of the embodiments disclosed, the preferred viscosity of the PFC liquid (at 25° C.) is greater than about 1.0 cSt. More preferably, the viscosity of the PFC liquid is greater than about 5.0 cSt. Most preferably, the viscosity of the PFC liquid is greater than about 7.0 cSt.

As discussed above with respect to several of the exemplary embodiments, the freezing point for the preferred fluorochemical liquid is below the freezing point of biological tissue. In several of these embodiments, it is preferable that the freezing point of the PFC liquid be less than about 0° C. More preferably, the freezing point of the PFC liquid is below about −40° C. In one preferred embodiment, the freezing point of the PFC liquid is less than about −50° C. In the embodiments where it is desirable to provide a PFC liquid that freezes during the cryogenic procedure, the PFC liquid preferably has a freezing point above the temperature produced by the cryoprobe. More preferably, the freezing point of the PFC liquid is above about 0° C. Most preferably, the freezing point of the PFC liquid is above about 5° C.

The preferred thermal conductivity of the PFC liquid for several of the disclosed embodiments is between about 0.50 and about 0.80 milliwatts/cm(°C.). More preferably, the thermal conductivity is between about 0.60 and 0.70 milliwatts/cm(°C.). Most preferably, the thermal conductivity is about 0.66 milliwatts/cm(°C.).

While the imaging techniques discussed hereinabove have concentrated on the use of ultrasound emitting equipment, other real-time imaging techniques are well within the purview of this invention. For example, radiographic techniques (e.g., fluoroscopic, computed tomography, etc.) and magnetic resonance imaging modalities may be used during cryosurgical procedures, especially with the advent of experimental near-real time interventional MR devices. Radiographic imaging would naturally be of greatest efficacy with radiopaque PFC liquids, e.g., Perflubron™ manufactured by Alliance Pharmaceuticals.

The present invention may be embodied in other specific forms without departing from the spirit or essential attributes thereof and, accordingly, reference should be made to the appended claims, rather than to the foregoing specification, as indicating the scope of the invention.

We claim:

1. A method for cryogenic treatment of a lesion comprising the steps of:
   (a) delivering a fluorochemical liquid to the lesion in order to facilitate the deterioration of the lesion:
   (b) placing at least one cryoprobe into the lesion; and
   (c) circulating cryogenic fluid through the cryoprobe, the cryogenic fluid causing cooling of a vicinity around the cryoprobe, the cooling causing the obliteration of at least a portion of the lesion.

2. A method for cryogenic treatment of a lesion according to claim 1 wherein the lesion is a lung lesion within a lung portion of biological tissue, the delivering process in step (a) comprises filling the lung portion with a fluorochemical liquid, and step (b) comprises placing the cryoprobe into the lung lesion.

3. A method for cryogenic treatment of a lesion according to claim 2 further comprising the step of monitoring the lung portion with a real-time medical imaging device during at least steps (b) and (c).

4. A method for cryogenic treatment of a lesion according to claim 3 wherein the imaging device is an ultrasound monitor.

5. A method for cryogenic treatment of a lesion according to claim 2 wherein the lung portion is filled with a fluorochemical liquid having a thermal conductivity less than that of the biological tissues, the fluorochemical liquid thereby acting to inhibit freezing of areas surrounding the cryoprobe.

6. A method for cryogenic treatment of a lesion according to claim 2 wherein the lung portion is filled with a fluorochemical liquid having a freezing point less than that of the biological tissues, the fluorochemical liquid thereby acting to promote freezing of areas surrounding the cryoprobe.

7. A method for cryogenic treatment of a lesion according to claim 2 wherein the lung portion is filled with a fluorochemical liquid having a thermal conductivity greater than that of the biological tissues, the fluorochemical liquid thereby acting to promote freezing of areas surrounding the cryoprobe.

8. A method for cryogenic treatment of a lesion according to claim 2 wherein the lung portion is filled by liquid ventilation.

9. A method for cryogenic treatment of a lesion according to claim 2 wherein the lung portion is filled by direct puncture of the lung portion and direct fluid instillation therethrough.

10. A method for cryogenic treatment of a lesion according to claim 2 wherein step (a) comprises filling the lung portion with a sufficient quantity of fluorochemical liquid to distend the lung portion.

11. A method for cryogenic treatment of a lesion according to claim 2 wherein before step (a), the method further comprises the steps of placing a balloon catheter into a lung bronchus, the lung bronchus leading to the lesioned lung portion, and occluding the bronchial lumen by inflating the balloon, the filling in step (a) comprising filling the lung portion with a fluorochemical liquid by flowing the fluorochemical liquid through the catheter.

12. A method for cryogenic treatment of a lesion according to claim 1 wherein the lesion is a pleural effusion in a pleural space, the delivery process in step (a) comprising filling the pleural space with a fluorochemical liquid, and step (b) comprises placing the cryoprobe into the pleural space, the method further comprising draining the pleural space of fluid therein before step (a), the cryogenic fluid causing cooling of the fluorochemical liquid in the pleural space to cause ablation of the tumor or inflammatory cells lining the plural space.

13. A method for cryogenic treatment of a lesion according to claim 1 wherein the lesion is a cyst, and wherein the delivery in step (a) comprises filling the cyst with a fluorochemical liquid, and step (b) comprises placing the cryoprobe into the cyst, the cryogenic fluid freezing and obliterating cells lining the cyst, the method further comprising the step of draining the cyst of any contents therein before step (a).

14. A method for cryogenic treatment of a lesion according to claim 13 wherein the cryoprobe includes at least one lumen and at least one outlet in fluid communication with the lumen, the cyst being drained and filled through the lumen and outlet.

15. A method for cryogenic treatment of a lesion according to claim 1 wherein the lesion is a vascular tumor site in an organ, and wherein the delivery in step (a) comprises filling the tumor site with a fluorochemical liquid, and step (b) comprises placing the cryoprobe into the tumor site, the method further comprising, prior to step (a), placing a first balloon catheter into an arterial passage leading to the tumor site, placing a second balloon catheter into a venous passage leading from the tumor site, and occluding the arterial and venous passage by inflating both of the catheter balloons, the tumor site being filled with the fluorochemical liquid by flowing the fluorochemical liquid through the catheter.

16. A method for cryogenic treatment of a lesion according to claim 1 wherein the lesion is within a hollow organ having a cavity therein, and wherein the delivery process in step (a) comprises filling the cavity with a fluorochemical liquid, the fluorochemical liquid penetrating the lesion and filling the area around the lesion.

17. A method for cryogenic treatment of a lesion according to claim 16 wherein before step (a), the method further comprises the steps of placing a balloon catheter into a passage leading into the hollow organ and occluding the passage by inflating the balloon, the filling in step (a) comprising filling the cavity with a fluorochemical liquid by flowing the fluorochemical liquid through the catheter.

18. A method for cryogenic treatment of a lesion according to claim 17 wherein the catheter includes a lumen, step (b) including the step of passing the cryoprobe through the lumen, into the cavity and into the lesion.

19. A method for cryogenic treatment of a lesion according to claim 1 wherein the lesion is within a portion of a duct, and wherein the delivery in step (a) comprises filling the duct portion with a fluorochemical liquid, the fluorochemical liquid penetrating the lesion and filling the area around the lesion.

20. A method for cryogenic treatment of a lesion according to claim 19 wherein before step (a), the method further comprises the steps of placing a balloon catheter into the duct and occluding the duct by inflating the balloon, the filling in step (a) comprising filling the duct portion with a fluorochemical liquid by flowing the fluorochemical liquid through the catheter.

21. A method for cryogenic treatment of a lesion according to claim 20 wherein the catheter includes a lumen, step (b) including the step of passing the cryoprobe through the lumen, into the duct and into the lesion.

22. A method for cryogenic treatment of a lesion according to claim 1 wherein the lesion is within a portion of an artery, and wherein the delivery process in step (a) comprises filling the artery portion with a fluorochemical liquid, the method further comprising, prior to step (a), placing a first balloon catheter into the arterial passage on one side of the artery portion, placing a second balloon catheter into the arterial passage on the other side of the artery portion, and isolating the arterial portion by inflating both of the catheter balloons, the arterial portion being filled with the fluorochemical liquid by flowing the fluorochemical liquid through the catheter.

23. A method for cryogenic treatment of a lesion according to claim 22 wherein the catheter includes a lumen, step (b) including the step of passing the cryoprobe through the lumen, into the artery portion and into the lesion.

24. A method for cryogenic treatment of a lesion according to claim 1 further comprising the step of monitoring the treatment with a real-time medical imaging device during at least steps (b) and (c).

25. A method for cryogenic treatment of a lesion according to claim 24 wherein the imaging device is an ultrasound monitor.

26. A method for cryogenic treatment of a lesion according to claim 1 wherein step (a) comprises delivering to the lesion a fluorochemical liquid having a sufficiently high thermal conductivity to enhance the formation of an ice ball.

27. A method for cryogenic treatment of a lesion according to claim 26 wherein step (a) comprises delivering to the lesion a fluorochemical liquid having a thermal conductivity greater than that of the biological tissues.

28. A method for cryogenic treatment of a lesion according to claim 1 wherein step (a) comprises delivering to the lesion a fluorochemical liquid having a freezing point greater than the temperature generated by the cryoprobe so as to enhance the formation of an ice ball.

29. A method for cryogenic treatment of a lesion according to claim 28 wherein the fluorochemical liquid has a freezing point greater than that of the biological tissues.

30. A method for cryogenic treatment of a lesion according to claim 1 wherein step (a) comprises delivering to the lesion a fluorochemical liquid having a thermal conductivity less than that of the biological tissues to inhibit the formation of an ice ball.

31. A method for cryogenic treatment of a lesion according to claim 30 wherein step (a) comprises delivering to the lesion a fluorochemical liquid having a thermal conductivity in a range from between about 0.60 and about 0.70 milliwatts/cm/°C.

32. A method for cryogenic treatment of a lesion according to claim 1 wherein step (a) comprises delivering to the lesion a fluorochemical liquid having a freezing point below about 0° C. to inhibit the formation of an ice ball.

33. A method for cryogenic treatment of a lesion according to claim 1 wherein the fluorochemical liquid has a freezing point less than that of the biological tissues to inhibit the formation of an ice ball.

34. A method for cryogenic treatment of a lesion according to claim 1 wherein the fluorochemical liquid is perfluorocarbon.

35. A method for cryogenic treatment of a lesion according to claim 1 wherein the cryoprobe includes at least one lumen and at least one outlet in fluid communication with the lumen, step (a) comprising delivering to the fluorochemical liquid to the lesion through the lumen and outlet.

36. A method for cryogenic treatment of a lesion according to claim 1 wherein step (a) comprises delivering to the lesion a fluorochemical liquid having a temperature below the temperature of the lesion, the fluorochemical liquid thereby aiding the development of an ice ball.

37. A method for cryogenic treatment of a lesion according to claim 1 wherein step (a) comprises delivering to the lesion a sufficient quantity of fluorochemical liquid to change its size or shape.

38. A method for cryogenic treatment of a lesion according to claim 1 further comprising delivering cooled fluorochemical liquid to the lesion through a first catheter and draining warmed fluorochemical liquid from the lesion through a second catheter during the treatment, wherein the cooled fluorochemical liquid enhances the formation of an ice ball.

39. A method for cryogenic treatment of a lesion according to claim 1 wherein step (a) comprises delivering the fluorochemical liquid to the lesion by direct injection into the lesion.

40. A method for cryogenic treatment of a lesion according to claim 1 wherein the lesion is within a portion of the uterus, and wherein the delivery in step (a) comprises filling a portion of the endometrial cavity and uterine cornua with a fluorochemical liquid, and step (b) comprises placing the cryoprobe into the endometrial cavity, the method further comprising, prior to step (a), occluding the uterine cornua and the cervical os for preventing leakage of the fluorochemical liquid, the cryoprobe causing cooling of the fluorochemical liquid in the endometrial cavity to cause ablation of the endometrial lining.

41. A method for cryogenic treatment of a lesion according to claim 1 wherein the lesion is located adjacent to a large vessel, and the delivery in step (a) comprises delivering the fluid between the lesion and the large vessel so as to produce pooling of the fluorochemical to force the tumor to separate from the large vessel.

42. A method for cryogenic treatment of a lesion according to claim 41 wherein the fluorochemical liquid has a thermal conductivity between about 0.60 and about 0.70 milliwatts/cm/°C.

43. A method for cryogenic treatment of a lesion according to claim 41 wherein the fluorochemical liquid has a freezing point less than the freezing point of biological tissue.

44. A method for cryogenic treatment of a lesion according to claim 1 wherein step (a) comprises delivering to the lesion a fluorochemical liquid having a temperature higher then the temperature of the lesion, the fluorochemical liquid thereby inhibiting the development of an ice ball.

45. A method for cryogenic treatment of a lesion according to claim 1 further comprising delivering warmed fluorochemical liquid to the tumor site through a first catheter and draining cooled fluorochemical liquid from the tumor site through a second catheter during the treatment, wherein the delivery of the warmed fluorochemical liquid inhibits the formation of an ice ball.

46. A method for cryogenic treatment of a lesion comprising the steps of:
(a) placing at least one cryoprobe into the lesion;
(b) circulating cryogenic fluid through the cryoprobe, the cryogenic fluid causing cooling of a vicinity around the cryoprobe resulting in the liquification of at least a portion of the lesion;
(c) draining at least a portion of the liquified material;
(d) delivering a fluorochemical liquid to the lesion after drainage; and
(e) circulating cryogenic fluid through the cryoprobe, the cryogenic fluid causing cooling of the fluorochemical liquid so as to further ablate the lesion, the fluorochemical liquid facilitating ablation of the lesion.

47. A method for cryogenic treatment of a lesion comprising the steps of:
(a) cooling a fluorochemical liquid to a temperature below the freezing temperature of biological tissue;
(b) placing a catheter in a vicinity of the lesion; and
(c) delivering the cooled fluorochemical liquid through the catheter to the vicinity of the lesion to obliterate at least a portion of the lesion, the fluorochemical facilitating obliteration of the lesion.

48. A method for cryogenic treatment of a lesion according to claim 47 further comprising the step of returning a warmed fluorochemical liquid from the lesion, the warmed fluorochemical liquid being recooled by a heat exchanger for subsequent delivery to the lesion.

49. A method for cryogenic treatment of a lesion according to claim 47 wherein the step of cooling the fluorochemical liquid comprises circulating the fluorochemical liquid through a heat exchanger.

50. A method for cryogenic treatment of a lesion according to claim 47 wherein the vicinity of the lesion includes a cavity and wherein the catheter is placed into the cavity.

51. A method for cryogenic treatment of a lesion according to claim 50 wherein the cavity is a endometrial cavity of a uterus and wherein the catheter directs the cooled fluorochemical liquid into the endometrial cavity.

52. A method for cryogenic treatment of a lesion according to claim 1 wherein the fluorochemical liquid has a viscosity above about 1 cSt and a freezing point below the freezing point of biological tissue.

53. A method for cryogenic treatment of a lesion according to claim 47 wherein the lesion is located adjacent to a large vessel, and the fluorochemical liquid delivery in step (c) comprises delivering the fluid between the lesion and the large vessel so as to produce pooling of the fluorochemical, the pooled fluorochemical liquid forcing the tumor to separate from the large vessel, and wherein the fluorochemical liquid has a viscosity greater than 1 cSt and a freezing point below the freezing point of biological tissue.

54. A method for cryogenic treatment of a lesion according to claim 47 wherein step (c) comprises delivering the fluorochemical liquid to the lesion by direct injection into the lesion.

55. A method for cryogenic treatment of a lesion according to claim 47 wherein the lesion is located within a portion of an artery and wherein the delivery in step (c) comprises filling the artery portion with a cooled fluorochemical liquid, the method further comprising, prior to step (c), placing a first balloon catheter into the arterial passage on one side of the artery portion, placing a second balloon catheter into the arterial passage on the other side of the artery portion, and isolating the arterial portion by inflating both of the catheter balloons.

56. A method for cryogenic treatment of a lesion according to claim 47 wherein the lesion is within a portion of a duct, and wherein the deliver in step (c) comprises filling the duct portion with a cooled fluorochemical liquid, the fluorochemical liquid thereby penetrating the lesion and filling the area around the lesion.

57. A method for cryogenic treatment of a lesion according to claim 47 wherein the lesion is located within a hollow organ having a cavity therein, and wherein the delivery in step (c) comprises filling the cavity with the cooled fluorochemical liquid, the cooled fluorochemical liquid penetrating the lesion and filling the area around the lesion, and wherein before step (c), the method further comprises the steps of placing a balloon catheter into a passage leading into the hollow organ and occluding the passage by inflating the balloon.

58. A method for cryogenic treatment of a lesion according to claim 47 wherein the lesion is a cyst, and wherein the delivery in step (c) comprises filling the cyst with the cooled fluorochemical liquid to obliterate the cells lining the cyst, the method further comprising the step of draining the cyst of any contents therein before step (a).

59. A method for cryogenic treatment of a lesion according to claim 47 wherein the lesion is a vascular tumor in an organ, and wherein the delivery in step (c) comprises filling the tumor site with a fluorochemical liquid, the method further comprising, prior to step (c), placing a first balloon catheter into an arterial passage leading to the tumor site, placing a second balloon catheter into a venous passage leading from the tumor site, and occluding the arterial and venous passage by inflating both of the catheter balloons.

60. A method for cryogenic treatment of a lesion according to claim 1 wherein the fluorochemical liquid has a viscosity greater than about 5 cSt.

61. A method for cryogenic treatment of a lesion comprising the steps of:

delivering the fluorochemical liquid into the vicinity of a lesion; and ablating at least a portion of the lesion by subjecting the lesion to a low temperature;

wherein the fluorochemical liquid facilitates the ablation of the lesion.

62. A method for cryogenic treatment of a lesion according to claim 61 wherein the fluorochemical liquid facilitates the ablation of the lesion by enhancing the cooling of the lesion.

63. A method for cryogenic treatment of a lesion according to claim 61 wherein the fluorochemical liquid facilitates the ablation of the lesion by inhibiting cooling of tissue surrounding the lesion.

64. A method for cryogenic treatment of a lesion according to claim 61 wherein the lesion is located within an organ having a cavity therein.

65. A method for cryogenic treatment of a lesion according to claim 64 wherein the organ is a lung.

66. A method for cryogenic treatment of a lesion according to claim 64 wherein the organ is a uterus.

* * * * *